United States Patent [19]

Eistetter

[11] 4,221,788

[45] Sep. 9, 1980

[54] 2-(OPTIONALLY-SUBSTITUTED)BENZYL-PERHYDROAZEPINES FOR ANALGESIA AND LOWERING BLOOD PRESSURE

[75] Inventor: Klaus Eistetter, Constance, Fed. Rep. of Germany

[73] Assignee: Byk Gulden Lomberg Chemische Fabrik GmbH, Constance, Fed. Rep. of Germany

[21] Appl. No.: 819,453

[22] Filed: Jul. 27, 1977

[30] Foreign Application Priority Data

Apr. 29, 1977 [LU] Luxembourg ............................... 229

[51] Int. Cl.$^2$ .................. C07D 223/04; A61K 31/395
[52] U.S. Cl. .................. 424/244; 260/239 B; 260/239 BF; 260/340.9 R
[58] Field of Search .................... 424/244; 260/239 B, 260/293.51, 293 BF, 340.9 R

[56] References Cited

U.S. PATENT DOCUMENTS 4,052,383  10/1977  Gold ................................. 260/239 B

OTHER PUBLICATIONS

Lee et al., Chem. Abs. 41, 6246i (1947).
Fery et al., Chem. Abs. 60, 15831e (1964).

*Primary Examiner*—Mark L. Berch
*Attorney, Agent, or Firm*—Berman, Aisenberg & Platt

[57] ABSTRACT

Title compounds and their acid-addition salts are physiologically acceptable or are readily converted to physiologically-acceptable counterparts by established procedures. They are pharmacologically active on the central nervous system (CNS) and are thus useful, when administered to warm-blooded animals, to induce central stimulation, to increase vigilance and to promote normal and pathologically-inhibited drive. They are also useful as analgesics and as blood-pressure-reducing agents for warm-blooded animals. These compounds are prepared, e.g., by reducing an appropriate 2-benzylazacycloheptane and are compounded into normal dosage-form medicament compositions.

47 Claims, No Drawings

2-(OPTIONALLY-SUBSTITUTED)BENZYLPERHYDROAZEPINES FOR ANALGESIA AND LOWERING BLOOD PRESSURE

RELATED APPLICATION

The subject matter of this invention bears a relationship to that of a concurrently-filed application (Ser. No. 819,460) having a common inventor.

BACKGROUND

In the course of work regarding elimination reactions, L.P.A. Fery and L. Wilputte-Steinert reported [Bull. Soc. Chim. Belg. 73 (1964) 154–165] the formation of 1-methyl-2-benzylhexamethylenimine without ascribing any useful activity to this compound. The compound was formed in such a small quantity that it could be identified only as a derivative in the form of the picrate and methiodide.

In German (laid-open) Patent Specification DT-OS No. 2,548,053 saturated α-substituted benzyl-1-benzhydrylazaheterocyclic compounds are claimed, but only α-substituted benzyl-1-benzhydrylazetidines are described; these are intended for use in treating obesity.

SUMMARY

2-Benzylperhydroazepines, which may be substituted one or more times by the same or different substituents on the phenyl and/or on the ring nitrogen, possess valuable and commercially useful pharmacological properties. A more limited aspect of the invention relates to 2-benzylperhydroazepines of formula A:

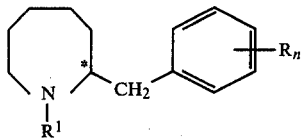

wherein $R^1$ is [methyl]$_{(2-a)}$[(—H)]$_{(2-b)}${(aliphatic hydrocarbyl having at least 2 carbon atoms)$_{(2-c)}$ [(alicyclic hydrocarbyl having from 3 to 7 ring carbon atoms)$_{(2-d)}${aralkyl$_{(2-t)}$[cycloalkylalkyl]$_{(t-1)}$}$_{(d-1)}$}$_{(c-1)}$}$_{(b-1)}$}$_{(a-1)}$; each R is [(—H)]$_{(a-1)}$[halo$_{(2-e)}${alkyl$_{(2-f)}$[(—OH)$_{(2-g)}$}{alkoxy$_{(2-h)}$[acyloxy$_{(2-i)}${(—NH$_2$)$_{(2-j)}$[-(monosubstituted amino)$_{(2-k)}${disubstituted amino)$_{(2-m)}$[(—NO$_2$)$_{(2-o)}${phenyl$_{(2-p)}$(substituted phenyl)$_{(p-1)}$}$_{(o-1)}$}$_{(m-1)}$}$_{(k-1)}$}$_{(j-1)}$}$_{(i-1)}$}$_{(h-1)}$}$_{(g-1)}$}$_{(f-1)}$}$_{(e-1)}$}$_{(2-a)}$;

n is a positive whole number of at most 4; each of
e, f, g, h, i, j, k, m, o and p is, independently for each occurrence of R, a positive whole number of at most 2; and
each of
a, b, c, d and t is, independently, a positive whole number of at most 2; and
to their acid-addition salts. All of the compounds of this invention are pharmacologically active. Those which are not physiologically acceptable are readily converted by art-recognized procedures to physiologically-acceptable counterparts. Physiological acceptability is readily determined by routine conventional testing.

The physiologically-acceptable compounds are conventionally incorporated as active ingredients in dosage-form medicament compositions with excipient and/or carrier normally employed for such purpose.

Throughout the disclosure and claims a number of terms appear and reappear. For convenience, a glossary of some of these terms and of their meanings, as used throughout this text, is provided.

acid-addition salt—a salt formed by a salt-forming group, such as a tertiary amine, and an acid, wherein the acid is, for example, an organic acid, e.g. tartaric acid; an inorganic acid, e.g. hydrochloric acid, hydrobromic acid and sulfuric acid; a monobasic acid, such as an alkanesulfonic acid, e.g. methanesulfonic acid ($H_3C$—$SO_3H$); a dibasic acid, e.g. succinic acid; a tribasic acid, e.g. phosphoric acid and citric acid; a saturated acid, e.g. acetic acid, an ethylenically-unsaturated acid, e.g. maleic acid and fumaric acid; and an aromatic acid, e.g. salicylic acid and arylsulfonic acids, such as benzenesulfonic acid; all references to organic or inorganic acids include the entire scope thereof unless otherwise limited. Pharmacologically-compatible salts of inorganic and of organic acids usually employed in Galenic practice are of primary interest. Pharmacologically-incompatible salts are readily converted into pharmacologically-compatible salts by conventional well-established processes. Illustrative pharmacologically-acceptable water-soluble and water-insoluble acid addition salts include the hydrochloride, hydrobromide, hydriodide, phosphate, nitrate, sulfate, acetate, citrate, gluconate, benzoate, hibenzate [2-(4-hydroxybenzoyl)benzoate], fendizoate [o-{(2'-hydroxy-4-biphenylyl)carbonyl}benzoate], propionate, butyrate, sulfosalicylate, maleate, laurate, malate, fumarate, succinate, oxalate, tartrate, amsonate [4,4'-diaminostilbene-2,2'-disulfonate], embonate [[1,1']methylene-bis-2-hydroxy-3-naphthoate], metembonate, stearate, tosilate [p-toluenesulfonate], 2-hydroxy-3-naphthoate, 3-hydroxy-2-naphthoate and mesilate [methanesulfonate], as well as salts with bumetanide [3-(butylamino)-4-phenoxy-5-sulfamoylbenzoic acid], furosemide [4-chloro-N-furfuryl-5-sulfamoylanthranilic acid], besunide [4-benzyl-3-butylamino-5-sulfamoylbenzoic acid], piretanide [4-phenoxy-3-(1-pyrrolidinyl)-5-sulfamoylbenzoic acid], etacrynic acid [{2,3-dichloro-4-(2-methylenebutyryl)phenoxy}acetic acid] and tienilic acid [{2,3-dichloro-4-(2-thenoyl)phenoxy}acetic acid].

acyl—a radical based on any organic acid, e.g. —CO—R*, wherein R* is, alicyclic hydrocarbyl (cycloalkyl, e.g. cyclohexyl), cycloalkylalkyl (e.g. cyclopropylmethyl), hydrocarbyl aralkyl (e.g. benzyl), hydrocarbyl aryl (e.g. phenyl) or, preferably, aliphatic hydrocarbyl (alkyl, e.g. methyl or ethyl).

acyloxy—an acyl radical (as previously defined) bound to another group through an oxygen bridge, especially —O—CO—$R^1$ and most suitably alkanoyloxy with from 1 to 7, more particularly with from 2 to 5, carbon atoms; acetoxy is the preferred acyloxy radical.

alicyclic—saturated, e.g. cycloalkyl, or aliphatically-unsaturated, e.g. cycloalkenyl, radicals having from 3 to 7 ring carbon atoms, such as cyclopropyl, cyclobutyl, cyclopentyl, cyclohexyl, cyclohexenyl and cycloheptyl, of which cycloalkyl, particularly those with 5 or 6 ring carbon atoms, are preferred.

aliphatic—an open-chain, linear or branched, substituted or unsubstituted, saturated or unsaturated (ethylenically, e.g. alkenyl, such as allyl, and/or acetylenically, e.g. alkinyl, such as propargyl) carbon-based radical (optionally having one or more hetero atoms and up to 7 carbon atoms unless otherwise specified), e.g. alkyl alkoxy and alkanoyl.

alkalize—render basic; adjust the pH to one which is in excess of 7.0, preferably 10 to 12.

alkenyl—both straight-chain and branch-chain mono- or poly-olefinically-unsaturated, preferably not more than di-olefinically-unsaturated, hydrocarbyl having a single available bond, having no triple bonds and containing from 3 to 7 carbon atoms unless otherwise limited, e.g. allyl, 2-methylallyl, buten-2-yl, penten-2-,3- or 4-yl, hexen-2-,3-,4- or 5-yl, hepten-2-,3-,4-,5- or 6-yl and pentadien-2,4-yl.

alkinyl—alkynyl; both straight-chain and branch chain unsaturated hydrocarbyl having at least one triple bond and from 3 to 7 carbon atoms, e.g. propin-2-yl.

alkoxy—alkyloxy and alkylenedioxy; alkyl bound to another group through an oxygen bridge, e.g. methoxy, ethoxy, propoxy, isopropoxy, butoxy, isobutoxy, secondary butoxy and tertiary butoxy. Those with from 1 to 4, and particularly with from 1 to 3, carbon atoms, especially methoxy, are preferred; also saturated (preferably straight-chain) aliphatic hydrocarbyl directly bound, by the same or different carbon atoms, to two oxygen atoms, each of which has an available bond, e.g. methylenedioxy, 1,2-ethylenedioxy, and 1,1-, 1,2- or 1,3-propylenedioxy or 2,2-dimethyl-1,3-propylenedioxy.

alkyl—straight-chain or branch-chain saturated aliphatic hydrocarbon radical having a single available bond and suitably containing from 1 to 7 carbon atoms, e.g. ethyl, propyl, isopropyl, butyl, secondary butyl, tertiary butyl, pentyl, hexyl, heptyl and, most advantageously, methyl, unless otherwise limited; straight-chain alkyl with from 1 to 6, particularly with from 1 to 4, and especially with from 1 to 3, carbon atoms are preferred. Branched alkyl radicals with from 3 to 7 carbon atoms are, e.g., isopropyl, isobutyl, sec.-butyl, tert.-butyl, 3-methylbutyl, 2,2-dimethylpropyl, 2-methylpentyl, 3,3-dimethylbutyl or 2-ethyl-3-methyl-butyl, of which those with from 3 to 5, especially with 3, carbon atoms are preferred.

alkylation—for the purpose of this disclosure "alkyl" of "alkylation" includes what is normally regarded as "alkyl" as well as all substituted alkyls, e.g. aralkyl and cycloalkylalkyl; it also includes alicyclic hydrocarbyl and, more specifically, cycloalkyl.

alkylenedioxy—a substituent which is a form of alkoxy wherein two oxygen atoms, each having an available bond, are directly bound to the same or different carbon atoms of saturated (preferably linear) hydrocarbyl; when the saturated hydrocarbyl is straight chain and has more than one carbon atom, the two oxygen atoms are preferably α,ω-bound thereto, as in 1,2-ethylenedioxy; when the two oxygen atoms are bound to the same carbon atom, as in 1,1-ethylenedioxy (ethylidenedioxy), the substituent is alternatively referred to as alkylidenedioxy; when this substituent is bound to a carbocyclic aromatic ring, it is necessarily bound to two different and preferably (but not necessarily) adjacent ring carbon atoms; when it is a substituent of the substituted benzyl ring of formula I, it takes the place of two R's, as in 3,4-methylene-dioxybenzyl.

amino—the H₂N-radical, which may be substituted by independently replacing one or both of the hydrogen atoms by a substituent, R; e.g. alkylamino and dialkylamino having from 1 to 4, preferably 1 or 2, carbon atoms in each alkyl and acylamino with the usual acyl groups, such as alkanoyl with from 2 to 5 carbon atoms, used to protect amino groups.

aralkyl—aryl-substituted alkyl wherein the aryl is hydrocarbyl (optionally-substituted) aryl having up to 12 ring carbon atoms, e.g. α-naphthyl, β-naphthyl, biphenylyl and, preferably, phenyl; and the alkyl (preferably methyl) advantageously has from 1 to 4 carbon atoms. Substituted or unsubstituted radicals wherein the aryl is phenyl, e.g. phenethyl, phenylpropyl and, especially, benzyl (or their nuclearly-substituted counterparts), are preferred.

aryl—a substituted or unsubstituted monovalent unsaturated aromatic carbocyclic radical having a single ring, e.g. phenyl, or 2 or 3 condensed rings, e.g. β-naphthyl and 3-acenaphthylenyl, having a total of at most 12 ring members; each aromatic ring having from 5 to 7 ring members; phenyl is preferred.

asymmetric carbon—a carbon atom, conventionally designated by an asterisk (*), which has four different radicals or atoms attached to it.

cycloalkyl—a saturated carbocyclic hydrocarbyl ring having from 3 to 7 ring carbon atoms, one of which has a single binding valence, e.g. cyclopentyl and cyclohexyl.

cycloalkylalkyl—alkyl having from 1 to 4, preferably 1 or 2, carbon atoms and substituted by cycloalkyl having from 3 to 7, preferably 3 to 5, ring carbon atoms. Illustrative examples are cyclopropylmethyl and cyclobutylmethyl.

free-base form—a compound or radical having at least one amino-nitrogen atom, and wherein each such nitrogen atom is a primary, secondary or tertiary amino nitrogen atom. In the subject disclosure reference is specifically to the ring nitrogen of a hexamethylenimine (e.g. one of formula A) substituted in the 2-position.

functional group—a group responsible for common properties.

functionalization—introduction or removal of a functional group, e.g. —OH, halo, (substituted or unsubstituted) amino, nitro, ether, ester, acyl, oxo or amide, into or from the molecular structure; introduction is illustrated by nitration, removal is illustrated by ether cleavage.

halo—fluoro, chloro, bromo or iodo; preferably fluoro, chloro or bromo, especially chloro.

hydrocarbyl—an organic (hydrocarbon) radical ordinarily (but not necessarily) having a single available bond and composed entirely of hydrogen and carbon atoms; such radicals are either substituted or unsubstituted, as specified; they are (saturated, ethylenically unsaturated and/or acetylenically unsaturated) aliphatic, (saturated or unsaturated) cycloaliphatic (i.e. alicyclic), cycloaliphaticaliphatic, homocyclic (single or multiple-condensed-ring) aromatic or aromaticaliphatic.

lower—restricts a radical to which it is applied to one having at most seven carbon atoms. Throughout the subject disclosure and claims all aliphatic, alkyl, alkoxy (including alkylenedioxy), acyl and acyloxy radicals are "lower" radicals (having at most 7 carbon atoms) unless otherwise specified.

radical—a group of atoms that behaves as a single atom in a chemical reaction or that remains unchanged during one or a series of reactions; throughout the instant disclosure a radical has only one binding valence bond unless otherwise defined.

substituted—bearing one or more substituents; the benzyl of 2-benzylperhydroazepines of formula A or I is nuclearly substituted by from 1 to 4 substituents, e.g. those designated R, $R^2$, $R^3$, $R^4$ and $R^5$; any aralkyl is optionally substituted [preferably nuclearly monosubstituted by, e.g., halo (p-chlorobenzyl, m-chlorobenzyl, p-bromobenzyl, o-fluorobenzyl or p-fluorobenzyl), alkyl having from 1 to 4 carbon atoms (p-methylbenzyl) or alkoxy having from 1 to 4 carbon atoms (p-methoxybenzyl) or substituted in the alkyl by, e.g., hydroxyl (4-hydroxy-4-phenylbutyl) or oxo {benzoylmethyl, 2-benzoylethyl, 3-benzoylpropyl, preferably 3-(p-chlorobenzoyl)propyl and particularly 3-(p-fluorobenzoyl)propyl}]; optionally-substituted phenyl is substituted, e.g., independently (at one or more positions) preferably by halo (p-chlorophenyl and p-fluorophenyl), hydroxyl (p-hydroxyphenyl), alkyl having from 1 to 4 carbon atoms (p-tolyl) or alkoxy having from 1 to 4 carbon atoms (p-methoxyphenyl); any contemplated substitution is either mono- or poly-substitution, the only limitation of which is steric hindrance, the conditions for which are well known and readily understood by every artisan.

substituted amino—substituents of mono (wherein one hydrogen atom of $-NH_2$ is replaced) or of di (wherein both hydrogen atoms of $-NH_2$ are replaced) -substituted amino include alkyl and acyl (particularly alkylamino having from 1 to 4, preferably 1 or 2, carbon atoms, dialkylamino having from 1 to 4, preferably 1 to 2, carbon atoms in each alkyl and acylamino, such as alkanoyl amino having from 2 to 5 carbon atoms), as well as the usual groups (tosyl, mesyl, anisyl, brosyl, nisyl, trityl, benzyl and benzyloxy-carbonyl) employed for protecting amino groups.

substituted aralkyl—optionally poly-, but preferably nuclearly mono-substituted by, e.g., halo (particularly fluoro, chloro or bromo), alkyl having from 1 to 4 carbon atoms and/or alkoxy having from 1 to 4 carbon atoms, e.g. p-chlorobenzyl, m-chlorobenzyl, p-bromobenzyl, o-fluorobenzyl, p-fluorobenzyl, p-methylbenzyl and p-methoxybenzyl. Substitution is additionally or alternatively in the alkyl of aralkyl as in arylhydroxyalkyl, e.g. 4-hydroxy-4-phenylbutyl, and in aryloxoalkyl, such as benzoylmethyl, 2-benzoylethyl, 3-benzoylpropyl, but preferably 3-(p-chlorobenzoyl)propyl and, in particular, 3-(p-fluorobenzoyl)propyl.

substituted phenyl—phenyl independently substituted in one or more available positions by halo, hydroxyl, alkyl having from 1 to 4 carbon atoms and/or alkoxy having from 1 to 4 carbon atoms; monosubstituted and p-substituted phenyl, such as p-chlorophenyl, p-fluorophenyl, p-hydroxyphenyl and p-methoxyphenyl, being preferred.

DETAILS

The invention relates to 2-benzylperhydroazepines which are optionally substituted one or more times (by the same or different substituents) in the phenyl ring, a process for their synthesis and pharmaceutical products containing them.

2-Benzylperhydroazepines are pharmacologically active and have a commercially-useful degree of pharmacological activity. Those compounds which may be regarded to have more than a desired degree of toxicity and/or side effects are readily converted to embodiments which lack such degree of toxicity and/or side effects, such as those of formula A and/or of the formula:

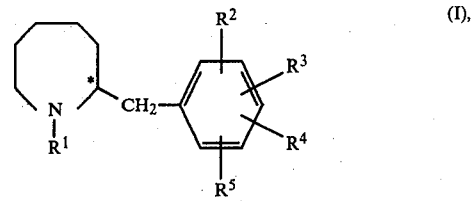

wherein
$R^1$ is a hydrogen atom (—H), aliphatic hydrocarbyl, alicyclic hydrocarbyl, cycloalkylalkyl or aralkyl; each of
$R^2$, $R^3$, $R^4$ and $R^5$ is, independently, a hydrogen atom (—H), halo, alkyl, hydroxyl (—OH), alkoxy, acyloxy, optionally-substituted amino, nitro (—NO$_2$) or optionally-substituted phenyl; or two of $R^2$, $R^3$, $R^4$ and $R^5$ are, together, alkylenedioxy; and their acid-addition salts. The acid-addition salts are preferably those which are physiologically acceptable, e.g. those regularly employed in medicinal preparations. Any acid-addition salt can be readily converted to the corresponding free base or to a different acid-addition salt by well-established processes known to the artisan.

In the compound aspect of this invention, the compound, 2-benzyl-1-methylperhydroazepine, and its acid-addition salts are expressly excluded. When $R^1$ is alkyl, it has at least 2, and preferably 3 or more, carbon atoms, i.e. when the benzyl ring is concurrently unsubstituted. When $R^1$ is methyl, it is preferred to have the benzyl nucleus substituted. When the benzyl nucleus is unsubstituted, $R^1$ is preferably hydrogen or cycloaliphaticaliphatic.

Compounds of this invention include those which, in free-base form, are of one of the formulae:

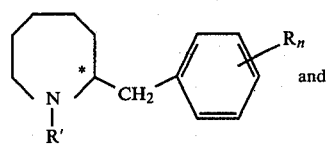

and

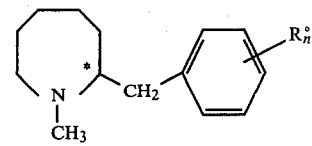

wherein
R' is a member selected from the group consisting of —H, lower aliphatic hydrocarbyl having more than one carbon atom, alicyclic hydrocarbyl having from 3 to 7 ring carbon atoms, optionally-substituted monoar(lower)alkyl and cycloalkyl(lower)alkyl; each R° is, independently, a member selected from the group consisting of halo, lower alkyl, —OH, lower alkoxy, acyloxy, —NH$_2$, monosubstituted amino, disubstituted amino, —NO$_2$, phenyl and substituted phenyl; or two, bound to adjacent ring carbon atoms, are jointly alkylenedioxy having from 1 to 4 carbon atoms; each R is —H, one of the independent meanings of R° or, together with another R, bound to an adjacent ring carbon atom, alkylenedioxy having from 1 to 4 carbon atoms;

n is a positive whole number of at most 4; and wherein any substituent bound to an aromatic carbon atom is a member selected from the group consisting of halo, lower alkyl, —OH, lower alkoxy, lower alkylenedioxy, lower alkanoyloxy, —NH$_2$, monosubstituted amino, disubstituted amino, —NO$_2$, phenyl and substituted phenyl; any substituent bound to an aliphatic carbon atom of an araliphatic radical is a member selected from the group consisting of —OH and oxo; and any substituent of monosubstituted or of disubstituted amino is, independently, a member selected from the group consisting of alkanoyl having from 2 to 5 carbon atoms and lower alkyl.

The preferred ring position of aromatically-bound substituents is that favored by conventional procedures. The only preclusion regarding positions of aromatically-bound substituents is that based on steric hindrance, as is readily appreciated by any artisan.

Of the compounds of formula I specific recognition is accorded those
wherein
$R^1$ is —H, straight-chained or branched aliphatic hydrocarbyl with from 1 to 6 carbon atoms, cycloalkylalkyl with 1 or 2 carbon atoms in the alkyl and from 3 to 5 carbon atoms in the cycloalkyl ring, or phenylalkyl with from 1 to 4 carbon atoms in the alkyl and, optionally, mono-substituted, preferably on the phenyl ring;
$R^2$ is halo, —OH, alkyl with from 1 to 4 carbon atoms, alkoxy with from 1 to 4 carbon atoms, alkanoyloxy with from 2 to 5 carbon atoms, —NH$_2$, dialkylamino with 1 or 2 carbon atoms in each alkyl, —NO$_2$, phenyl or p-substituted phenyl; each of
$R^3$, $R^4$ and $R^5$ is, independently, —H, halo, —OH, alkyl with from 1 to 4 carbon atoms, alkoxy with from 1 to 4 carbon atoms, alkanoyloxy with from 2 to 5 carbon atoms, —NH$_2$, dialkylamino with 1 or 2 carbon atoms in each alkyl or —NO$_2$; two of
$R^2$, $R^3$, $R^4$ and $R^5$, alternatively, are together alkylenedioxy having from 1 to 4 carbon atoms; particularly those wherein one or both of the 2- and 6-positions of the benzyl nucleus are unsubstituted, and their pharmacologically acceptable acid-addition salts. Of these, preferred 2-benzylperhydroazepines are those
wherein
$R^1$ is —H, straight-chained alkyl with from 1 to 3 carbon atoms, branched alkyl with from 3 to 5 carbon atoms, cycloalkylmethyl with from 3 to 5 ring carbon atoms in the cycloalkyl, benzyl, p-halobenzyl, p-methylbenzyl or p-methoxybenzyl;
$R^2$ is halo, —OH, methoxy, —NH$_2$ or —NO$_2$;
$R^3$ is —H, halo, —OH, methoxy, —NH$_2$ or —NO$_2$; each of
$R^2$ and $R^3$ is, preferably, in one of the 2-, 3- and 4-positions; each of
$R^4$ and $R^5$ is —H; and their pharmacologically-acceptable acid-addition salts. Selected compounds from this group include those wherein $R^1$ is —H, methyl, isopropyl, cyclopropylmethyl or benzyl. From these selected compounds those are especially preferred
wherein
$R^1$ is —H, methyl, isopropyl or cyclopropylmethyl;
$R^2$ is 2-chloro, 3-chloro, 4-chloro or 4-amino; and each of
$R^3$, $R^4$ and $R^5$ is —H; and their pharmacologically-acceptable acid-addition salts.

Special attention is also accorded those compounds of formula I
wherein
$R^1$ is —H, straight-chained or branched aliphatic hydrocarbyl with from 2 to 6 carbon atoms, cycloakylalkyl with 1 or 2 carbon atoms in the alkyl and from 3 to 5 carbon atoms in the cycloalkyl ring, phenalkyl with from 1 to 4 carbon atoms in the alkyl or mono-substituted, preferably nuclearly, phenalkyl; each of
$R^2$, $R^3$, $R^4$ and $R^5$ is, independently, —H, halo, —OH, alkyl with from 1 to 4 carbon atoms, alkoxy with from 1 to 4 carbon atoms, alkanoyloxy with from 2 to 5 carbon atoms, —NH$_2$, dialkylamino with 1 or 2 carbon atoms in each alkyl, —NO$_2$, phenyl or p-substituted phenyl;
the benzyl nucleus being unsubstituted in at least one of the 2- and 6-positions, and the corresponding pharmacologically-acceptable acid-addition salts. Of these, preferred 2-benzylperhydroazepines are those
wherein
$R^1$ is —H, straight-chained alkyl with 2 or 3 carbon atoms, branched alkyl with from 3 to 5 carbon atoms, cycloalkylmethyl with from 3 to 5 ring carbon atoms in the cycloalkyl, benzyl, p-halobenzyl, p-methylbenzyl or p-methoxybenzyl; each of
$R^2$ and $R^3$ is, independently, —H, halo, —OH, methoxy, —NH$_2$ or —NO$_2$ and is preferably in the 2-, 3- or 4-position; and each of
$R^4$ and $R^5$ is —H; and
their pharmacologically-acceptable acid-addition salts. Select 2-benzylperhydroazepines of this group are those in which $R^1$ is —H, ethyl, isopropyl, cyclopropylmethyl or benzyl, and the corresponding pharmacologically-acceptable acid-addition salts.

Of all of the previously-noted compounds of formula I and their corresponding pharmacologically-acceptable acid-addition salts particular note is made of those in which at least one and preferably each of at least two of $R^3$, $R^4$ and $R^5$ is —H and the benzyl nucleus is unsubstituted in one or both of the o-positions.

Selected compounds according to the invention are:
2-(2-chlorobenzyl)-1-methylperhydroazepine,
2-(4-chlorobenzyl)perhydroazepine,
2-(4-chlorobenzyl)-1-isopropylperhydroazepine,
2-(4-chlorobenzyl)-1-methylperhydroazepine,
2-(4-aminobenzyl)perhydroazepine,
2-benzylperhydroazepin,
2-benzyl-1-cyclopropylmethylperhydroazepin,
2-[3-isobutoxy-5-methylbenzyl]-1-methylperhydroazepine,
1,2-dibenzylperhydroazepine,
1,2-di-(p-chlorobenzyl)perhydroazepine,
2-(4-acetoxy-3-nitrobenzyl)-1-ethylperhydroazepine,
1-cyclohexyl-2-(3,4-methylenedioxybenzyl)perhydroazepine,
2-(4-fluorobenzyl)-1-isopropylperhydroazepine, 1-allyl-2-(3-isopropyl-5-methoxybenzyl)perhydroazepine,
2-(4-aminobenzyl)-1-propargylperhydroazepine,
2-[3,5-dichloro-4-(p-methoxyphenyl)benzyl]-1-cyclohexyl perhydroazepine,
1-cyclopropylmethyl-2-(4-amino-3-chloro-2-methylbenzyl) perhydroazepine, and
their pharmacologically-compatible acid-addition salts.

The 2-benzylperhydroazepines of formulae A and I process a chirality center on the carbon atom marked with an (*). The invention therefore includes the racemates, the individual enantiomers and their mixtures.

SYNTHESIS

2-Benzylperhydroazepines are prepared, e.g., according to one of the hereinafter-presented procedures from available starting materials or from starting materials which are produced from known compounds according to established or art-recognized procedures. According to one procedure:

(A) a 2-benzyl-azacycloheptane of the general formula II

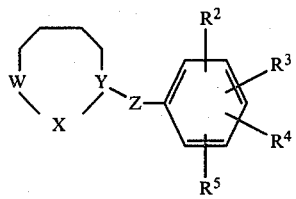

in which $R^2$, $R^3$, $R^4$ and $R^5$ have the previously-ascribed meanings;

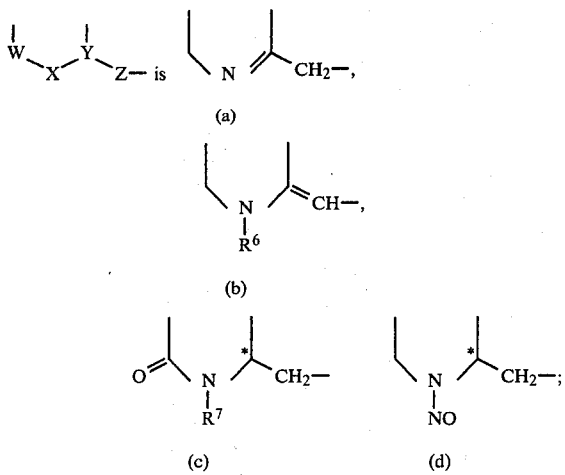

$R^6$ is aliphatic hydrocarbyl, alicyclic hydrocarbyl, cycloalkylalkyl or aralkyl; and
$R^7$ is —H, aliphatic hydrocarbyl, alicyclic hydrocarbyl or cycloalkylalkyl
is reduced and, if desired, then N-alkylated or N-dealkylated and/or functionalized, and/or the obtained free base or its acid-addition salt is conventionally converted from one to another.

According to a second procedure:
(B) a 2-benzylazacycloheptane of formula III

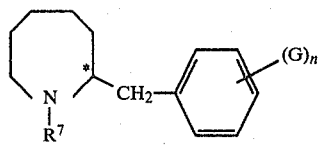

wherein
$R^7$ has its previously-ascribed meaning;
G is —H or a precursor of a functional group; and
n is a whole number from 1–4, inclusive, preferably 1 or 2, especially 1;
is functionalized and, if desired, then N-alkylated or N-dealkylated, and/or the obtained free base or its acid-addition salt is conventionally converted from one to another.

According to a third procedure:
(C) an N-acyl-2-benzyl-azacyclopentane of formula IV

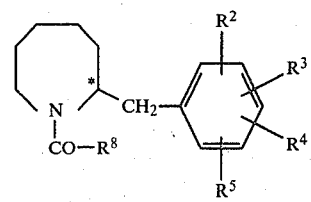

wherein
$R^2$, $R^3$, $R^4$ and $R^5$ have their previously-ascribed meanings; and
$R^8$ is aliphatic hydrocarbyl, alicyclic hydrocarbyl, cycloalkylalkyl, optionally-substituted phenyl or optionally-substituted phenalkyl;
is reduced and, if desired, then functionalized and/or N-dealkylated, and/or the obtained base or its acid-addition salt is conventionally converted from one to another.

The reduction of the substituted 2-benzyl-azacycloheptanes of formula II a, b and d is preferably carried out with hydrogen in organic solvent (conventionally employed in hydrogenation reactions), e.g. ethanol, methanol, cyclohexane, isopropanol and dimethylformamide, in the presence of or in contact with metallic catalyst, e.g. platinum, platinum on active carbon, palladium, palladium on active carbon and Raney nickel, under a pressure of from about 1 to 500 atomspheres and at a temperature around room temperature, for example within the range of from 0° to 50° C. The reduction of compounds of formulae II a and II b is alternatively carried out with such compounds in the form of their acid-addition salts in aqueous alcoholic solution with sodium borohydride in a conventional manner (cf. "Enamines: Synthesis, Structure and Reactions", edited by A. Gilbert Cook, pages 185 et seq., MARCEL DEKKER, New York and London, 1969). The reduction of compounds IIc is effected with lithium aluminum hydride in inert solvent, such as an ether, e.g. diethyl ether, tetrahydrofuran, dioxan, 1,2-dimethoxyethane or diethyleneglycol diethyl ether, at temperatures between 0° C. and the boiling temperature of the solvent, preferably between 20° C. and 70° C. The reduction of compounds II d is effected alternatively by reaction with hydrogen halide, preferably hydrogen chloride, in inert solvent, e.g. benzene, in analogy to the process described in Synthesis, 1976, 540–41.

Starting compounds of formula IIa

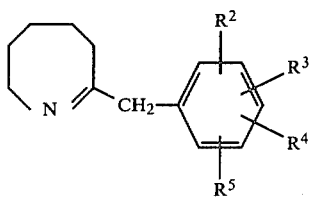

(IIa), in which $R^2$, $R^3$, $R^4$ and $R^5$ have their previously-ascribed meanings, are obtained, e.g., by reacting a corresponding 2-benzylideneazacycloheptane of formula V

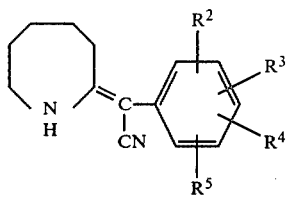

(V), in which $R^2$, $R^3$, $R^4$ and $R^5$ have their previously-ascribed meanings, with strong mineral acid. The hydrolysis and simultaneous decarboxylation of nitriles V are carried out with mineral acid, such as hydrochloric acid, hydrobromic acid or sulfuric acid, preferably with concentrated hydrochloric acid, at a temperature between room temperature (20° C.) and 120° C., preferably by heating the relevant solution under reflux until the evolution of carbon dioxide ceases. The resultant imines IIa are relatively unstable compounds, and their prompt processing, e.g. hydrogenation to form perhydroazepines, is strongly recommended.

Benzylidene compounds V are obtained, for example, according to the process described by T. Kametami and others [J. Chem. Soc., Perkin I, 1976, 389; Heterocycles 3(1975) 691], by which a caprolactim ether, preferably caprolactim methyl ether, is reacted with a corresponding arylacetonitrile, for example 4-chlorophenylacetonitrile, in the presence of an auxiliary base, such as diazabicycloundecene, diazabicyclononene, triethylamine or ethyldiisopropylamine, either without solvent or in an inert solvent, such as benzene, toluene, xylene or cyclohexane, at a temperature of from 50° to 150°, preferably at from 100° to 130°, and optionally under an inert gas, e.g., nitrogen. The reaction is preferably effected without using an inert solvent.

The initial compounds IIB are prepared according to various processes. For example, they are obtained by reacting an N-substituted caprolactam derivative VI with a phenylacetic acid derivative VII to form the corresponding benzylidene compound VIII, their hydrolysis and decarboxylation according to the following reaction scheme:

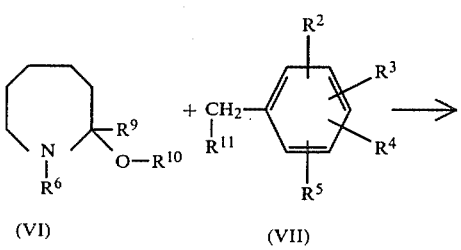

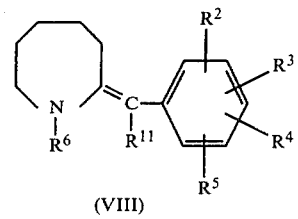

(VIII)

VIII ⟶ IIb wherein
$R^2$, $R^3$, $R^4$, $R^5$ and $R^6$ have their previously-ascribed meanings:
$R^9$ is —O—$R^{12}$ or

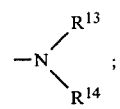

;

$R^{11}$ is —CN or —CO—O—$R^{15}$; each of
$R^{10}$, $R^{12}$, $R^{13}$, $R^{14}$ and $R^{15}$ is, independently, alkyl having from 1 to 5 carbon atoms, preferably methyl or ethyl;
$R^{14}$ is, alternatively, phenyl; and
$R^9$ and —O—$R^{10}$, jointly, alternatively represent alkylenedioxy with from 1 to 4, preferably 2, carbon atoms.

The reaction of a caprolactam derivative VI with a phenylacetic acid derivative VII is generally carried out at a temperature of from 20° to 150° C., preferably between 40° and 100° C., without or preferably with the addition of inert organic solvent, such as aliphatic hydrocarbon, for example petroleum ether, light petrol or ligroin, cycloaliphatic hydrocarbon, for example cyclohexane; or aromatic hydrocarbon, for example benzene, toluene or xylene. The hydrolysis and simultaneous decarboxylation of a benzylidene derivative VIII (ester or acetonitrile) are carried out by the action of mineral acid, such as hydrochloric acid or hydrobromic acid, preferably concentrated hydrochloric acid, at a temperature between room temperature and 120° C., preferably by heating the relative solution under reflux until the evolution of $CO_2$ ceases. Enamines IIb resulting from esters or corresponding acetonitriles VIII are relatively unstable compounds and are advantageously further processed immediately, i.e. hydrogenated to form compounds of formula A. Because of their stability and their easy accessibility and also because of the instability of enamines IIb, esters VIII (or the corresponding acetonitriles) constitute interesting and valuable intermediate products for the production of 2-benzylperhydroazepines I according to the invention.

N-substituted caprolactam derivatives VI are known compounds or are obtained by recognized processes from known starting materials.

Acid amideacetal VI ($R^9$: —O—$R^{12}$) is obtained, for example, by reacting N-alkylcaprolactam with an alkylating agent, such as dimethylsulfate, diethylsulfate or alkyl p-toluenesulfonate, to form salt IX ($R^9$: —O—$R^{12}$) and subsequently reacting the latter with alkali metal alcoholate, such as sodium methylate or ethylate. Aminal ester VI ($R^9$: —$NR^{13}R^{14}$) is obtained by reacting salt IX ($R^9$: —$NR^{13}R^{14}$) with alkali metal alcoholate, such as sodium methylate or ethylate, in inert solvent, such as benzene or an ether, for example diethyl ether.

Initial compounds IIb) are obtained by reacting an azepinium salt IX with a phenylacetic acid derivative VII in the presence of strong base to form a benzylidene compound VIII, its subsequent hydrolysis and decarboxylation in accord with the following equation:

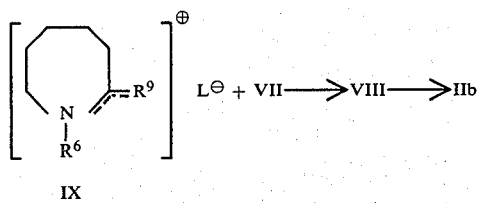

in which $R^6$ and $R^9$ have their previously-ascribed meanings, and $L^\ominus$ is an equivalent of an anion of an organic or inorganic acid.

The reaction of an azepinium salt IX with a phenylacetic acid derivative VII usually takes place without the addition of further solvent in the presence of strong base, such as a solution of alkali metal alcoholate, for example sodium methylate, potassium methylate, potassium propylate, sodium isopropylate, potassium butylate, potassium tert.-butylate, potassium tert.-pentylate or, especially, sodium ethylate, at a temperature of from 20° to 150° C., preferably at from 80° to 100° C. If desired, the reaction is carried out while passing through an inert gas, such as nitrogen, in order to remove any volatile amine which is formed. However, the reaction is optionally carried out with the addition of inert solvent, such as an alcohol, for example methanol, ethanol, propanol, isopropanol, butanols, pentanols; a tertiary nitrogen base, for example pyridine; or a hydrocarbon, for example benzene. The hydrolysis and decarboxylation of a benzylidene compound VIII is carried out analogously to the previously-described processes.

The production of a salt IX, of which that in which $R^9$ is $—NR^{13}R^{14}$ is preferred, is carried out, for example, in analogy to the process of H. Bredereck and others (Chem. Ber., 1964, 3081) by the reaction of a corresponding N-substituted caprolactam with an alkylating agent, such as diethylsulfate, methyliodide or, preferably, dimethylsulfate, in inert solvent at from room temperature to 120° C., preferably without solvent at a temperature of around 80° C., and, when (in the salt IX) $R^9$ represents $—NR^{13}R^{14}$, subsequent reaction with an amine $HNR^{13}R^{14}$, or optionally by reacting a corresponding caprolactam with inorganic acid chloride, such as phosphorus oxide chloride or phosgene, followed by reaction with an amine $HNR^{13}R^{14}$ in an inert solvent, such as benzene, at a temperature between 0° and 100° C., preferably between 20° and 60° C., or without solvent at a temperature between 0° and 100° C., preferably between 40° and 80° C.

The initial compounds IIc are obtained according to methods known in the art. Starting compounds IIc wherein $R^7$ is a hydrogen atom are obtained, e.g., by rearrangement of the corresponding 2-benzylcyclohexanones according to the process described by T. Duong et al. [Austr. J. Chem., 29 (1976) 2667–82, particularly page 2681]. They are also obtained by functionalization of 7-benzylhexahydroazepin-2-one according to methods described in the following paragraphs. Starting materials IIc, wherein $R^7$ is an aliphatic hydrocarbyl, an alicyclic hydrocarbyl, a cycloalkylalkyl or an aralkyl, are obtained by N-alkylation of the corresponding 7-benzylhexahydroazepin-2-ones. A convenient method, e.g., is described by T. Duong et al. [Austr. J. Chem., 29 (1976) 2651–65, particularly page 2660].

The initial compounds IId are obtained, for example, by lithiation of 1-nitrosoperhydroazepin and subsequent reaction with corresponding benzyl halides, preferably bromides or iodides, in accordance with the process described in Synthesis, 1976, 540–41.

Functionalization of a 2-benzylperhydroazepine III or the optional subsequent functionalization of a 2-benzylperhydroazepine I obtained by reduction is carried out according to the nature of the substituents ultimately desired in the phenyl group.

The nitro group is introduced, for example, by nitration with nitric acid, nitric acid/sulfuric acid, potassium nitrate/sulfuric acid or alkyl nitrate at a temperature from $-20°$ to $+50°$ C., preferably at from $-20°$ to $+30°$ C. In initial compounds III, G then signifies a hydrogen atom and $n=1$; in the end products each of $R^2$, $R^4$ and $R^5$ is a hydrogen atom and $R^3$ is an $NO_2$ group in the p-position. Under more severe conditions dinitro compounds are obtained; each of $R^4$ and $R^5$ is a hydrogen atom, and each of $R^2$ and $R^3$ is a nitro group.

The amino group is introduced by reduction (of the $NO_2$ group or groups of a corresponding nitro-substituted compound) with hydrogen over a suitable catalyst, such as Pt, Pt/C, Pd, Pd/C or Raney nickel in a conventional solvent, such as alcohol or cyclohexane. In an initial compound III, G is $—NO_2$ and $n=1$ or 2; in a corresponding end product each of $R^4$ and $R^5$ is a hydrogen atom and $R^2$ and/or $R^3$ is $—NH_2$.

Halogen atoms, especially chlorine and bromine atoms, are introduced in the conventional way by halogenation of the ring. For ring halogenation catalysts, e.g. iron, ferric chloride, ferric bromide, aluminum chloride, aluminum bromide, tin tetrachloride or iodine, are used, the reaction being carried out without solvent or in inert solvents. Ring halogenation is alternativey effected in glacial acetic acid without a catalyst at a temperature between 0° and 20° C.

Hydroxy groups are introduced by ether splitting of correspondingly-positioned alkoxy groups. In initial compounds III, G then signifies an alkoxy group, preferably a methoxy group, and $n=1$ to 4, preferably 2, especially 1. Ether splitting is carried out, for example, by boiling with hydriodic acid or hydrobromic acid or mixtures of hydrobromic acid/glacial acetic acid or by reaction with boron tribromide in inert solvent, such as chloroform or dichloromethane, at a temperature of from $-20°$ to $20°$ C.

Etherification is carried out, for example, by reacting corresponding hydroxy compounds (G in initial compounds III is then a hydroxy group; $n=1$ to 4, preferably 2, especially 1) with alkyl halide in the presence of an equivalent quantity of alkali metal alcoholate, for example sodium ethylate.

Functionalization of free hydroxy groups or of amino groups in the form of acylation or an, optionally, successive acylation is carried out according to methods known to the technician, for example by reaction with a corresponding acid anhydride or halide (cf., inter alia, Houben Weyl, Vol. 8, pages 543 et seq. or 655 et seg.). Splitting off of an acyl group with the liberation of a hydroxy group or an amino group is carried out in the usual manner by saponification, for example by reaction with a suitable base, such as caustic soda or potash.

N-alkylation, in which "alkyl" also includes cycloalkyl, aralkyl and cycloalkylalkyl, is carried out by conventional methods known to the technician. Thus, N-alkylation is carried out with an alkylating agent, such as an alkyl halide, an alkyl sulfonate (for example tosylate), or an alkylsulfate, in inert solvent, such as acetone, methylethylketone, an alcohol (such as methanol, ethanol or isopropanol) or dimethylformamide or without solvent, using an auxiliary base, such as sodium carbonate, potassium carbonate or triethylamine, at a temperature from about 20° to 100° C.

N-de-alkylation, in which "alkyl" also includes cycloalkyl, cycloalkylalkyl and aralkyl, especially benzyl, is conventionally carried out according to known methods, for example with a chloroformate ester, such as ethyl chloroformate, $\beta,\beta,\beta$-trichloroethyl chloroformate, without or in the presence of inert solvent, such as benzene, toluene or chloroform, at an elevated temperature, preferably at the boiling point of the solvent. The obtained intermediate product is reacted with an aqueous or alcoholic solution of base, such as caustic soda/ethanol or caustic potash/butanol, at an elevated temperature, preferably at the boiling point of the solvent, to form the corresponding de-alkylperhydroazepine, i.e. to form a corresponding compound of formula I in which $R^1$ is a hydrogen atom.

N-de-alkylation in the special form of de-benzylation, i.e. when using a compound of formula I in which $R^1$=benzyl, is alternatively carried out by catalytic hydrogenolysis with a catalyst, preferably palladium on carbon, in a solvent, such as methanol, ethanol, benzene or cyclohexane, at a temperature of from 0° to 50° C., preferably room temperature, and at a hydrogen pressure of from 1 to 300 atmospheres, preferably at from 1 to 5 atmospheres.

An acid-addition salt is obtained by dissolving a free base in a suitable solvent, for example acetone, water, a low-molecular aliphatic alcohol (e.g. ethanol or isopropanol) or ether (e.g. diethyl ether or tetrahydrofuran) which contains the desired acid, or to which the desired acid is subsequently added. The salt is recovered by filtration, precipitation with a non-solvent for the addition salt or by evaporation of the solvent.

The obtained salt, for example the hydrochloride, is converted into the free base by neutralization with aqueous sodium or potassium hydroxide, and the base is then recovered by solvent extraction, using a suitable solvent, such as chloroform, dichloromethane, diethyl ether, benzene, toluene or cyclohexane, which is not miscible with water. A free base is also obtained by neutralization of an acid-addition salt with sodium methylate in methanol and isolation of the base using conventional known processes. An acid-addition salt is also converted into another acid-addition salt, for example a pharmacologically-compatible acid-addition salt, by conversion into the corresponding base followed by further reaction with an appropriate acid.

Any necessary or desired racemate splitting is carried out conventionally, for example by mixing with an optically-active acid, such as mandelic acid, tartaric acid, camphorsulfonic acid or dibenzoyltartaric acid, recrystallization of the resultant salt until the specific rotation is constant and liberating the optically-active base with alkali. The other enantiomer is obtained in an analogous fashion from the mother liquor.

Reduction of an N-acyl-2-benzylazacycloheptane of formula IV is conventionally effected according to known methods, for example by reaction with a complex metallic hydride, as reducing agent, in an anhydrous organic solvent and hydrolytic working up. Suitable reducing agents include lithium aluminum hydride (lithium hydridoaluminate) as well as sodium dihydrido-bis-(2-methoxyethoxy)aluminate. A suitable solvent is, e.g., inert anhydrous ether, such as diethyl ether, tetrahydrofuran, dioxan, 1,2-methoxyethane or diethleneglycoldiethylether, as well as aromatic hydrocarbon, such as benzene or toluene, or a mixture of two or more of these compounds. The temperature of the reaction is not critical and can vary within wide limits, for example from 0° to 100° C. The reaction is ordinarily advantageously effected at reflux temperature for the reaction mixture. The duration of the reaction depends upon the reaction temperature used and may vary between about 1 hour and 24 hours. At the preferred reflux temperature the reaction normally ends in from 3 to 4 hours. The reactants are used, e.g., in equivalent quantities, but having an excess of reducing agent is preferred. After the reaction the reaction product is then processed by treating the reaction mixture with an aqueous medium, such as water, dilute aqueous inorganic acid or base or other media containing water. The product is optionally isolated as free base or as an acid-addition salt by appropriately adjusting the pH.

The starting compounds of the general formula III are obtained, for example, by de-methylation of 2-benzyl-1-methylperhydroazepin (to III, wherein $R^1$:—H) and optionally subsequent N-alkylation (to III wherein $R^1$: alkyl, cycloalkyl, aralkyl, cycloalkylalkyl).

An initial compound of formula IV is also produced by conventional methods known to the technician, for example by acylation of a corresponding 2-benzylperhydroazepine I ($R^1$=—H) with a carboxylic acid halide, such as Cl—CO—$R^8$ in which $R^8$ has its previously-ascribed meaning, e.g. acetyl chloride, propionyl chloride, butyryl chloride, pivaloyl chloride, cyclopropylcarbonyl chloride, cyclobutylcarbonyl chloride, benzoyl chloride or phenylacetyl chloride, or with a carboxylic acid anhydride in inert solvent, such as benzene, toluene, cyclohexane, chloroform or dichloromethane, in the presence of an auxiliary base, such as pyridine or triethylamine, at a temperature between 0° and 50° C.

Intermediate products of formualae A and I are converted by known methods into pharmacologically-effective compounds of formulae A and I, as set out in the examples which follow. Acid-addition salts are thus obtained from free bases by reaction with a corresponding acid. Ethers, i.e. those compounds in which one or more of the substituents $R^2$, $R^3$, $R^4$ amd $R^5$ are alkoxy or two neighboring substituents $R^2$, $R^3$, $R^4$ and $R^5$ jointly represent alkylenedioxy, are converted by acid hydrolysis, for example with hydrogen halide, into a corresponding free-hydroxy compound. Esters, i.e. those compounds in which one or more of the substituents $R^2$, $R^3$, $R^4$ and $R^5$ represent acyloxy, are converted by alkaline hydrolysis, for example with sodium hydroxide, into a corresponding free-hydroxy compound. The free hydroxy compounds, i.e. those in which one or more of the substituents $R^2$, $R^3$, $R^4$ and $R^5$ are -OH, are etherified or esterified.

UTILITY

Optionally-substituted 2-benzylperhydroazepines of formulae A and I possess valuable and commercially-useful properties. These compounds, 2-benzyl-1-methylperhydroazepin and their pharmacologically-, i.e. biologically-, tolerable salts possess pronounced pharmacological properties, particularly with regard to the central nervous system (CNS), to blood pressure and to sensation of pain in warm-blooded animals, e.g. mammals, particularly human beings. They are also converted into other 2-benzylperhydroazepines of formulae A and I, and therefore represent valuable intermediates in the synthesis of pharmacologically-active compounds of formula I or of their biologically-tolerable salts.

The activity on the CNS of 2-benzylperhydroazepines and their pharmacologically-tolerable salts extends to central stimulation, to increase in vigilance and to promotion of normal and pathologically-inhibited drive of warm-blooded animals. In addition, some embodiments display a strong analgesic action or a blood-pressure regulating action in warm-blooded animals afflicted with pathological irregularities in blood pressure.

The excellent and broad pharmacological efficacy of the 2-benzylperhydroazepines permits their use both in human and in veterinary medicine, where they are used for prophylaxis of disorders or for treatment of symptoms which have already appeared.

Lack of drive, reduction in vigilance, depression, organic psychosyndromes in cerebral degeneration processes, lack of performance, blood pressure disorders, conditions of exhaustion, and conditions of pain in men or women and mental and psychological inhibition of development and difficulties in studying in children are indications for use of these compounds in human medicine.

So far as veterinary medicine is concerned, the indications are: drop in performance and conditions of pain. For example: higher animals, such as farm and domestic animals, are advantageously treated with these compounds.

MEDICAMENT COMPOSITIONS AND ADMINISTRATION

The present invention includes pharmaceutical compositions and products having as the sole pharmacologically-active ingredient (or as one of a combination of pharmacologically-active ingredients) a compound (or a mixture of compounds) of formula A, a compound (or a mixture of compounds) of formula I and/or a pharmacologically-acceptable acid-addition salt of either.

Preferred pharmaceutical products are those which contain one or more 2-benzylperhydroazepines of one of the previously-presented more-limited groups of embodiments or their preferred representatives and/or the corresponding pharmacologically-compatible acid-addition salts.

The pharmaceutical products are prepared according to conventional processes. As pharmaceutical products the new compounds are used as such or, optionally, in combination with one or more suitable pharmaceutical-support substances. When a new pharmaceutical preparation contains pharmaceutical-support substance in addition to active principle, the active-principle content of the mixture is from 5 to 95, preferably from 25 to 75, percent by weight of the total mixture.

According to the invention the active principle is used in human or veterinary medicine in any desired form; it is administered systemically or topically in a manner which ensures formation or maintenance of adequate blood or tissue levels or local concentrations of the 2-benzylperhyroazepine. This is effected either by oral, rectal or parenteral administration in suitable doses. However, the pharmaceutical products are also administerable locally. Pharmaceutical preparations of the active principle are more advantageously provided in the form of unit doses, which are designed for the particular administration desired. A unit dose consists, for example, of a tablet, a pill, a capsule, a suppository or a measured volume of a powder, a granulate, a solution, an emulsion, a suspension, a sol or a gel.

The term "unit dose", within the meaning of the present invention, is a physically-determined unit which contains an individual quantity of the active component in combination with pharmaceutical support. The active principle content corresponds to a fraction or a multiple of a therapeutical individual dose. An individual dose preferably contains the quantity of active principle which is dispensed in a single application and which usually corresponds to a whole, a half, a third or a quarter of a daily dose. When, for an individual therpeutical administration, only a fraction, such as a half or a quarter, of the unit dose is required, the unit dose is advantageously divisible, for example in the form of a tablet with a notch.

The pharmaceutical preparations according to the invention, when they are in unit-dose form and are intended for administration, for example, to man, contain from about 1 to 200, advantageously from 2.5 to 100 and especially from 5 to 50 milligrams (mg) of active principle.

In general, it is advantageous (both in human medicine and also in veterinary medicine) to administer the active principle or principles (in the case of oral administration) in a daily dose of from about 0.06 to about 12, preferably from 0.14 to 5.7 and especially from 0.3 to 3, mg/kilogram (kg) of body weight, optionally in the form of a number, preferably from 1 to 3, of individual doses so as to achieve the desired results. An individual administration contains the active principle or principles in quantities of from about 0.01 to about 3.0, preferably from 0.04 to 1.5 and especially from 0.07 to 0.7, mg/kg of body weight.

For parenteral treatment, for example of acute depression or of severe pain, similar dosages are used. In the case of this therapy, about 1 to about 50 mg of active principle are administered.

For local administration a preparation in a pharmacologically-acceptable, e.g., aqueous solution which contains from about 0.1 to about 5, preferably from 0.2 to 3 and especially from 0.5 to 2, percent by weight of active principle is used.

Therapeutic administration of a pharmaceutical preparation according to this invention (in the case of long term medication) is generally effected at fixed times such as from 1 to 4 times a day, for example after meals and/or in the evening. For acute attacks the medication is administered at varying points of time, as required. Under certain circumstances it is necessary to vary from the noted dosages in view of the nature, the body weight and the age of the patient under treatment, the nature and severity of the disorder, the nature of the preparation and the mode of administration of the pharmaceutical product, as well as the interval within which plural administrations take place. Thus in some cases it is sufficient to manage with less than the noted amount of active principle, while other cases call for a larger amount of active principle. The determination of the optimum dose and form of administration of active principle necessary for each case is made, when required, by those charged with this responsibility according to established conventional techniques.

The pharmaceutical preparations generally consist of active principle according to the invention and non-toxic pharmaceutically-compatible pharmaceutical support. The support is used in the form of an admixture with or a diluent for the active principle; it is in solid, semi-solid or liquid form. The support is optionally in the form of an enrobing agent, for example in the form of a capsule, a tablet coating, a bag or another container, for the therapeutically-active component. A support material serves, for example, as a carrier for the active principle through the body, as a formulation aid, as a sweetener, as a taste corrector, as a coloring agent or as a preservative.

Administration dosage forms include, e.g., tablets, pills, hard and soft capsules (for example of gelatin), dispersible powder, granulates, aqueous and oily suspensions, emulsions, solutions or syrups.

Tablets optionally contain inert diluent, for example calcium carbonate, calcium phosphate, sodium phosphate or lactose; granulating and distributing agent, for example maize starch or alginate; binder, for example starch, gelatin or acacia gum; and lubricant, for example aluminum stearate, magnesium stearate, talcum or silicone oil. In addition, tablets are optionally provided with a coating, e.g. one which ensures delayed solution and resorption of the pharmaceutical product in the gastrointestinal tract and consequently, for example, improved compatibility, protraction or retarding effect. Gelatin capsules optionally contain the pharmaceutical product mixed with a solid diluent (for example calcium carbonate or kaolin) or an oil diluent (for example olive oil, groundnut oil or liquid paraffin).

Aqueous suspensions optionally contain suspending agent (for example sodium carboxymethylcellulose, methylcellulose, hydroxypropylcellulose, sodium alginate, polyvinylpyrrolidone, gum dragon or acacia gum), dispersant and wetting agent (for example polyoxyethylene stearate, heptadecaethylene oxycetanol, polyoxyethylene sorbitol monooleate, polyoxyethylene sorbitan monooleate or licithin), preservative (for example methyl or propyl hydroxybenzoates), flavoring, and sweetener (for example saccharose, lactose, sodium cyclamate, dextrose or invert sugar syrup).

Oily suspensions optionally contain groundnut oil, olive oil, sesame oil, coconut oil or liquid paraffin and thickener, such as beeswax, hard paraffin wax or cetyl alcohol; they may also contain sweetener, flavoring and anti-oxidant.

Powders and granulates (which are dispersible in water) optionally contain the pharmaceutical principle mixed with dispersing, wetting or suspending agent, for example those previously mentioned, as well as with sweetener, flavoring and coloring agents.

Emulsions optionally contain olive oil, groundnut oil or liquid paraffin as well as emulsifier, such as acacia gum, gum dragon, phosphatide, sorbitan monooleate or polyoxyethylene sorbitan monooleate, sweetener and flavoring.

Suppositories are used for rectal administration of the pharmaceutical products. These are produced with the aid of binder which melts at rectal temperature, for example cocoa butter or polyethyleneglycol.

Aqueous suspensions for sterile injection, isotonic saline solutions or other solutions which contain dispersant or wetting agent and/or pharmacologically-compatible diluent, for example propyleneglycol or butyleneglycol, are used for parenteral administration of the pharmaceutical products.

Gels, sols or tablets suitable for local treatment optionally contain (in addition to the active principle or principles) conventional support material, for example animal or vegetable fat, wax, paraffin, starch, gum dragon, cellulose derivatives, polyethyleneglycol, silicone, bentonite, silica, talcum, zinc oxide or a mixture of two or more of these substances.

Powders and sprays optionally contain (in addition to the active principle or principles) conventional support material, such as lactose, talcum, silica, aluminum hydroxide, calcium silicate, polyamide powder or a mixture of two or more of these substances. In addition, sprays optionally contain conventional propellant, for example chlorofluorinated hydrocarbon.

If desired, the active principle or principles are provided in a microencapsulated form with one or more of the previously-mentioned support materials.

In addition to the 2-benzylperhydroazepin, pharmaceutical preparations within the scope of this invention optionally contain one or more pharmacologically-active, chemically- and physiologically-compatible components belonging to other groups of pharmaceutical products, for example mild stimulant (such as caffein), analgesic (such as aminophenazone, acetylsalicyclic acid or d-propoxyphene), anti-depressives (such as dibenzepin, doxepin, matrotilin, amitriptylin, nortriptyline or melitracene), tranquilizer (such as meprobamate, benzodiazepines, e.g. diazepam, chlordiazepoxide), and/or substance for promoting cerebral circulation and/or roborifacient (such as glutamic acid, vitamins or combinations thereof).

Compounding procedures for and actual formulations used in preparing pharmaceutical compositions containing one or a combination of 2-benzylperhydroazepines or their pharmacologically-acceptable acid-addition salts are conventional and known to all technicians in the pharmaceutical compounding art. Only the subject active principle is different.

A further aspect of the invention concerns treating mammals suffering from primary or secondary disorders of the central nervous system, from pain or from pathological variations in blood pressure. A CNS-effective, an analgesic-active or a blood pressure-regulating and pharmacologically-compatible amount of one or more 2-benzylperhydroazepines and/or their pharmacologically-tolerated salts is administered to such mammals.

PHARMACOLOGY

The pharmacological properties, e.g. central stimulation, reserpine antagonism, tremorine antagonism, analgesic action, anticataleptic effect and anti-hypertensive activity, of the compounds according to the invention are clearly demonstrable on albino mice and albino rats. In the subsequent Tables, each investigated compound is assigned an identification number according to the following enumeration:

| compound No. | Name of compound |
|---|---|
| 1 | 2-benzyl-1-cyclopropylmethylperhydroazepin |
| 2 | 2-benzylperhydroazepin |
| 3 | 2-benzyl-1-methylperhydroazepin |
| 4 | 2-(4-chlorobenzyl)-1-isopropylperhydroazepin |
| 5 | 2-(4-aminobenzyl)perhydroazepin |
| 6 | 2-(4-chlorobenzyl)perhydroazepin |

-continued

| compound No. | Name of compound |
|---|---|
| 7 | 2-(3,4-dimethoxybenzyl)-1-methylperhydroazepin |
| 8 | 2-(4-chlorobenzyl)-1-ethylperhydroazepin |
| 9 | 1-allyl-2-(4-chlorobenzyl)perhydroazepin |
| 10 | 2-(2-chlorobenzyl)-1-methylperhydroazepin |
| 11 | 2-(4-chlorobenzyl)-1-hexylperhydroazepin |
| 12 | 2-(4-chlorobenzyl)-1-methylperhydroazepin |

Compounds according to the invention are distinguished by central stimulation, which is reflected in an increase of vigilance and excitability; in rarer cases, also in mild promotion of motor activity. The results of behaviour investigations on the albino mouse are reproduced in Table I.

TABLE I

| Increase of vigilance and excitability | | | Additional increase of activity | | |
|---|---|---|---|---|---|
| Compound No. | mg/kg orally | Intensity | Compound No. | mg/kg orally | Intensity |
| 1 | 1 | ++ | 1 | 25–50 | ++ |
| 2 | 10 | ++ | 5 | 12 | ++ |
| 3 | 20 | +(+) | 8 | 25 | + |
| 4 | 20 | ++ | 4 | 50 | + |
| 5 | 20 | ++ | | | |
| 6 | 25 | +(+) | | | |
| 7 | 25 | + | | | |
| 8 | 50 | + | | | |
| 9 | 50 | + | | | |
| 10 | 50 | + | | | |
| 11 | 100 | (+) | | | |

Intensity scale:
++ greatly increased
+(+) very distinctly increased
+ distinctly increased
(+) mildly increased The compounds according to the invention have a particularly strong reserpine-antagonistic activity. This antagonism is demonstrable in the case of prophylactic and therapeutic administration. In Table II the $ED_{50}$ values according to investigations on the albino mouse are reproduced.

TABLE II (a) Prophylactic administration to the mouse

| Compound No. | Abolition of ptosis [mg/kg orally] | Promotion of drive [mg/kg orally] |
|---|---|---|
| 10 | 17 | 9 |
| 1 | 22 | 12 |
| 5 | 20 | 16 |
| 6 | 12 | 19 |
| 4 | 22 | 24 |
| 12 | 30 | 23 |
| 2 | 35 | 45 |
| 9 | 38 | 43 |
| 8 | 58 | 50 |
| 7 | 70 | 45 |
| 3 | ~75 | ~60 |

(b) Therapeutic administration to the mouse

| Compound No. | Abolition of ptosis [mg/kg orally] | Promotion of drive [mg/kg orally] |
|---|---|---|
| 2 | 45 | 18 |
| 1 | ~50 | ~10 |
| 6 | 110 | ~20 |
| 10 | ~75 | ~75 |
| 5 | 65 | 100 |

Compounds according to the invention have prophylactic activity against the formation of a catalepsy caused by haloperidol. In Table III the $ED_{50}$ values according to investigations on the albino mouse are reproduced.

TABLE III

| Compound No. | [mg/kg orally] |
|---|---|
| 2 | ~30 |
| 11 | ~40 |
| 5 | ~50 |
| 8 | ~60 |

Compounds according to the invention have prophylactic activities against the formation of the tremor and hypersalivation caused by tremorine. In Table IV the $ED_{50}$ values according to investigations on the albino mouse are reproduced.

TABLE IV

| | Inhibition of | |
|---|---|---|
| Compound No. | tremor [mg/kg orally] | hypersalivation [mg/kg orally] |
| 12 | 21 | 25 |
| 4 | 31 | 100 |
| 9 | 55 | 120 |
| 8 | 50 | 70 |
| 2 | 67 | 85 |
| 6 | 65 | ~100 |
| 5 | 45 | >100 |
| 11 | 90 | 70 |

For compounds according to the invention, analgesic effects are evidenced in various analgesic models on the albino mouse.

In Table V the $ED_{50}$ values (calculated from the dose effect curves) are presented.

TABLE V (a) Tail-flick test

| Compound No. | [mg/kg orally] |
|---|---|
| 2 | ~5 |
| 3 | ~10 |
| 9 | 15 |
| 6 | 16 |
| 5 | 20 |
| 4 | 25 |
| 8 | 30 |
| 10 | 50 |

(b) Writhing test (acetic acid)

| Compound No. | [mg/kg orally] |
|---|---|
| 5 | 40 |
| 8 | 45 |
| 6 | ~50 |
| 4 | ~50 |
| 9 | ~50 |

Compounds according to the invention cause a reduction of blood pressure in the anaesthetised normotonic albino rat. Table VI presents data reflecting the maximum lowering of blood pressure [in mm of Hg] in the range of the first 5 minutes and 20 minutes after intravenous administration of a dose of 10 mg/kg.

TABLE VI

| | Lowering of blood pressure [mm Hg] | |
|---|---|---|
| Compound No. | Max. [5 min. after administration] | 20 min. after administration |
| 2 | 37 | 26 |
| 6 | 23 | 22 |
| 4 | 22 | 22 |

TABLE VI-continued

| Compound No. | Lowering of blood pressure [mm Hg] | |
|---|---|---|
| | Max. [5 min. after administration] | 20 min. after administration |
| 1 | 20 | 16 |
| 5 | 12 | 20 |
| 7 | 39 | 24 |

The determination of the pharmacological properties was effected according to the following methods:

1. Behaviour

To observe the behaviour of albino mice, in each instance 5 animals were kept in a Makrolon cage, Type II. A comparative assessment vis-a-vis untreated controls was made. Vigilance and increase of motor activity were assessed from the behaviour of the undisturbed mice; the increased excitability was assessed from the reaction to outer stimuli, such as noise and contact, in comparison with the reacting of the control animals.

2. Reserpine antagonism

Subcutaneous application of 2 mg/kg of reserpine causes ptosis [Domenjos and Theobald (1959), Arch. Int. Pharmacodyne., 120/450] in albino mice in the course of several hours; also, the normal movement activity of the animal (drive) ("Reserpine Drive Inhibition") [Sulser, Bickel and Brodie, Med. Exp., 5, 454, 1961] is considerably inhibited. The intensity of both symptoms was graded by a rating scale: 0-1-2-3, by which the degree of the effect (from no effect to complete ptosis, and from no inhibition to complete inhibition of drive) is reflected. These experiments were conducted both under prophylactic and under therapeutic administration of the test substances. The substances tested antagonized the symptoms in a dose-dependent manner. The $ED_{50}$ of the antagonistic effect was evaluated in comparison with the daily control. Arch. Int. Pharmacodyn.

3. Haloperidol antagonism

Subcutaneous administration of haloperidol (7.5 mg/kg) causes catalepsy in albino mice. The cataleptic behaviour of the animals was tested by placing the animals on a wire cradle bridge for 30 seconds [Julou, L., Bardone, M.-C., Ducrot, R., Laffargue, B., and Loiseau, G., "Neuro-Psycho-Pharmacology, "International Congress Series No. 129, 293–303, 1967]. The substances tested prevented, in a dose-dependent manner, the occurrence of catalepsy after application of haloperidol. The dose which inhibited the occurrence of catalepsy in 50% of the animals is determined.

4. Tremorine antagonism

Intraperitoneal application of tremorine (12.5 mg/kg) causes tremor and hypersalivation in albino mice lasting about 30 minutes. The intensity of both symptoms was graded by a points systems: 0-1-2, [no effect (0%), slight effect, strong effect (100%)], by which the degree is reflected. The substances tested antagonized the symptoms in dependence on the dose. The antagonistic effect of preventively given doses was evaluated. The doses which inhibited the occurrence of the tremor and hypersalivation in 50% of the animals within the range of 10 to 20 minutes after tremorine administration were determined. Literature: Everett, G.M., Nature, 177 (1956) 1238.

5. Analgesia (a) Tail flick test [D'Amour, F.E.; and Smith, D. L., J. Pharmacol. Exp. Ther., 72, 74, 1941]: a thermal pain was applied to female albino mice on the tail root with a focused heat ray and the time until the tail is drawn away was recorded with a stopwatch. Normally, the time is in the range of 4 to 5 seconds. The substances caused delayed reaction of the thermal pain, i.e. a reduced reaction to thermal pain. The dose which prolonged the reaction time by 50% was determined. F.E., and Smith, D.L., (1941) J. Pharmacol, Exp. Ther., (b) Writhing [Koster, Anderson and De Beer, Fed. Proc. 18, 412, 1959]test (acetic acid writhing): intraperitoneal injection of 0.2 ml/20 g of mouse body weight of a 0.75 percent (v/v) acetic acid solution induces (in albino mice) a typical syndrome, called "writhing", proceeding over the body with dorsal flection. These writhes (occurring in the course of the first half hour after administration) were counted over the a period of from 5 to 20 minutes after administration. The substances tested caused a decrease in the number of writhing syndromes. The dose which reduces the writhes by 50% with reference to the daily control was determined.

6. Blood pressure determinations

The substances were administered intravenously to normotone albino rats (Sprague Dawley; male) which have been anaesthetised with chloralose (80 mg/kg intraperitoneally). The blood pressure measurement was effected in the A. carotis dexter by means of a Statham pressure recorder; the measurement of the heart frequency was effected with EKA pulse rate meter. The body temperature was kept constant to 37.5°±0.2° C. by warming with an incandescent lamp which was controlled via a rectal temperature sensor. Registration was effected continuously over one hour p.a. The maximum of the effect within the first 5 minutes and of the effect after 20 minutes were determined.

Specific Embodiments

The following examples illustrate the invention in greater detail without restricting it. The abbreviation MP signifies melting point, BP signifies boiling point, dec. signifies decomposition. The temperatures are given in °C.

EXAMPLE 1

2-dimethylamino-1-methyl-4,5,6,7-tetrahydro-3H-azepinium methylsulfate

Stir 190 g of N-methylcaprolactam and 189 g of dimethylsulfate for 3 hours at 80° C. Cool the resulting reaction mixture to ambient temperature before shaking it with diethyl ether and then freeing it from solvent residue in vacuo to obtain 346 grams (g) of 2-methoxy-1-methyl-4,5,6,7-tetrahydro-3H-azepinium methylsulfate as a light yellow oil. Add this oil, drop by drop, to a solution of 110 g of dimethylamine in 600 milliliters (ml) of benzene while stirring and boil the thus-prepared admixture under reflux for 90 minutes. Collect the heavy phase and extract it several times with diethyl ether. Concentrate the produced yellowish oil in vacuo to obtain 336 g (93% of theory) of the title compound.

EXAMPLE 2

2-(α-ethoxycarbonyl-4-chlorobenzylidene)-1-methyl-perhydroazepine

Add (drop by drop at 90° in a stream of nitrogen to let the alcohol escape) a solution of 4.6 g of sodium in 100 ml of ethyl alcohol to a mixture of 53.2 g of the title compound of Example 1 and 29.8 g of ethyl 4-chlorophenylacetate. Stir it for a further 4 hours at 90° and then cool it to ambient temperature. Mix the cooled reaction mixture with 100 ml of water and 100 ml of diethyl ether, collect the organic phase and dry the latter over sodium sulfate. Concentrate the dried organic phase and then distil off any excess ethyl 4-chlorophenylacetate under a high vacuum to obtain a crude yield [15.5 g (34% of theory)] of the title compound as yellow oil.

EXAMPLE 3

2-(α-ethoxycarbonyl-3,4-dimethoxybenzylidene)-1-methylperhydroazepine

Follow the procedure of Example 2 to obtain 8.6 g (17% of theory) of the title compound as a viscous yellow oil with a BP of 175° to 180° (0.001 mm of Hg) from 53.2 g of the title compound of Example 1, 33.6 g of ethyl 3,4-dimethoxyphenylacetate and a solution of 4.6 g of sodium in 100 ml of ethyl alcohol.

EXAMPLE 4

2-(α-ethoxycarbonyl-4-methoxybenzylidene)-1-methylperhydroazepine

Follow the procedure of Example 2 to obtain 15.6 g (34% of theory) of the title compound as a viscous yellow oil with a BP of 165° (0.001 mm of Hg) from 53.2 g of the title compound of Example 1, 29.1 g of ethyl 4-methoxyphenylacetate and a solution of 4.6 g of sodium in 100 ml of ethanol.

EXAMPLE 5

2-(α-ethoxycarbonyl-3-methoxybenzylidene)-1-methylperhydroazepine

Follow the procedure of example 2 to obtain 38.6 g (65% of theory) of the title compound in the form of a viscous oil from 74.9 g of the title compound of Example 1, 40 g of ethyl 3-methoxyphenylacetate and a solution of 6.4 g of sodium in 160 ml of ethanol.

EXAMPLE 6

2-(4-chlorobenzyl)-1-methylperhydroazepine

Boil 15.5 g of 2-(α-ethoxycarbonyl-4-chlorobenzylidene)-1-methylperhydroazepine and 110 ml of concentrated hydrochloric acid under reflux until the evolution of $CO_2$ ceases. Cool the resulting reaction mixture to ambient temperature; then alkalize it with caustic soda solution (while cooling with ice) and extract the product with diethyl ether. Concentrate the ether phase and dry the prepared concentrate over sodium sulfate. Dissolve the residual 2-(4-chlorobenzylidene)-1-methylperhydroazepine (7.44 g) in ethyl alcohol and hydrogenate with platinum/active carbon/hydrogen. Filter the catalyst from the hydrogenated product, distil off the solvent and then distil the remainder under a high vacuum to obtain 4.4 g of the title compound with a BP of 102° to 110° at 0.003 mm of Hg.

The picrate (from ethyl alcohol) melts at 120° to 121°.

The reaction of the title base with an equivalent quantity of the corresponding acid gives the following salts:
Hibenzate: colorless oil
Citrate: colorless oil
Fumarte: light yellow oil
Benzoate: light yellow oil
Maleate: light yellow oil
Embonate: yellow oil

EXAMPLE 7

2-(3,4-dimethoxybenzyl)-1-methylperhydroazepine

Follow the procedure of Example 6 to obtain the title compound with a BP of 117° at 0.001 mm of Hg from 12.28 g of the title compound of Example 3.

The picrate (from ethyl alcohol) melts at 127° to 129°.

EXAMPLE 8

2-(α-cyanobenzylidene)perhydroazepine

Stir 8.1 g of caprolactim methyl ether and 5.0 g of benzyl cyanide with 0.6 g of 1,5-diazabicyclo [5.4.0]undec-5-ene under nitrogen for 48 hours at 130°; distil off any excess benzyl cyanide under a high vacuum, and rub down the thus-produced residue with a little methyl alcohol before filtering to obtain 3.78 g of the title compound. Recrystallize from methyl alcohol to obtain a purer product, MP 108° to 113°.

EXAMPLE 9

2-(α-cyano-4-chlorobenzylidene)perhydroazepine

Agitate a mixture of 5.0 g of 4-chlorobenzyl cyanide, 5.5 g of caprolactim methyl ether and 0.5 g of diazabicyclo [5.4.0]undec-5-ene under nitrogen for 18 hours at 125°. Cool the thus-obtained reaction mixture to ambient temperature and then rub down the crystallizing residue with 20 ml of methyl alcohol before filtering to obtain 5.5 g of the title compound. Recrystallize this compound from methyl alcohol to obtain a product with a MP of 114° to 117°.

EXAMPLE 10

2-(4-chlorobenzyl)perhydroazepine

Boil 100 g of the title compound of Example 9 in 1 liter of concentrated hydrochloric acid under reflux until the evolution of carbon dioxide ceases. Cool the thus-prepared reaction mixture to ambient temperature. Alkalize the cooled reaction mixture with caustic soda solution (while cooling with ice) and then extract the product with diethyl ether. Dry the ether extract over sodium sulfate and then concentrate it.

(a) Hydrogenate the thus-obtained 2-(4-chlorobenzyl)-4,5,6,7-tetrahydro-3H-azepine with platinum/active carbon/ hydrogen. Filter out the catalyst, concentrate the filtrate and distil to obtain 61.9 g (68% of theory) of the title compound with a BP of 93° at 0.1 mm of Hg.

(b) Dissolve the thus-obtained 2-(4-chlorobenzyl)-4,5,6,7-tetrahydro-3H-azepin in diluted hydrochloric acid (pH~5) and mix it with 200 ml of methyl alcohol. Add 7 g of sodium borohydride in small portions within 20 minutes, keeping the pH-value constant by occasional addition of hydrochloric acid. Stir for 1 hour, render alkaline with caustic soda solution and extract with dichlormethane. Dry the organic phase over sodium sulphate, concentrate and distil to obtain 58 g of the title compound with a BP of 93° at 0.1 mm Hg.

The hydrochloride (from methyl alcohol/diethyl ether) melts at 177° to 178°.

EXAMPLE 11

2-benzylperhydroazepine

Follow the procedure of Example 10 to obtain 7.46 g (56% of theory) of the title compound with a BP of 88° at 0.007 mm of Hg from 15 g of the title compound of Example 8 and 177 ml of concentrated hydrochloric acid.

The hydrochloride (from methyl alcohol/diethyl ether) melts at 164° to 167°.

EXAMPLE 12

1-ethyl-2-(4-chlorobenzyl)perhydroazepine

Boil together (under agitation) 4 g of 2-(4-chlorobenzyl)perhydroazepine, 2.5 g of anhydrous potassium carbonate and 2.9 g of ethyl bromide under reflux for 26 hours in 30 ml of ethylmethylketone. Cool the thus-produced reaction mixture to ambient temperature. Mix the cooled reaction mixture with water and then extract it with diethyl ether. Dry the resulting organic phase over sodium sulfate, remove the ether and distil the residue to obtain 5.12 g (70% of theory) of the title compound with a BP of 112° at 0.005 mm of Hg.

EXAMPLE 13

1-allyl-2-(4-chlorobenzyl)perhydroazepine

Follow the procedure of Example 12 to obtain 6.76 g (72% of theory) of the title compound with a BP of 110° at 0.02 mm of Hg from 8 g of the title compound of Example 10, 5 g of anhydrous potassium carbonate and 8.7 g of allyl bromide.

EXAMPLE 14

2-(4-chlorobenzyl)-1-isopropylperhydroazepine

Follow the procedure of Example 12 to obtain 3.9 g (56% of the theory) of the title compound with a BP of 113° at 0.03 mm of Hg from 5.8 g of the title compound of Example 10, 3.6 g of anhydrous potassium carbonate and 6.6 g of isopropyl iodide.

EXAMPLE 15

2-(4-chlorobenzyl)-1-hexylperhydroazepine

Follow the procedure of Example 12 to obtain 3.87 g (56% of theory) of the title compound with a BP of 129° at 0.005 mm of Hg from 5 g of the title compound of Example 10, 3.1 g of anhydrous potassium carbonate and 4 g of 1-bromo-hexane.

EXAMPLE 16

2-(4-nitrobenzyl)perhydroazepine

Add (drop by drop while stirring at −10°) 10 g of 2-benzylperhydroazepine to 43 ml of concentrated sulfuric acid. Then, at the same temperature, add 33 ml of concentrated nitric acid to the thus-prepared reaction mixture and allow it to heat slowly to room temperature. Stir it for a further hour. Pour the resulting admixture into 500 g of ice, alkalize it with 6 N caustic soda solution and then extract it with diethyl ether. Dry the organic phase over sodium sulfate and distil off the solvent from the dried organic phase to obtain 12.0 g (97% of theory) of the title compound as a red oil.

EXAMPLE 17

2-(4-aminobenzyl)perhydroazepine

Hydrogenate 12 g of the title compound of Example 16 in 300 ml of ethyl alcohol with platinum/hydrogen. After the absorption of hydrogen has ceased, filter off the catalyst and concentrate the filtrate to obtain 10.5 g (100% of theory) of the title compound as a dark brown viscous oil.

The benzoate (from isopropyl alcohol) melts at 186° to 190° (dec.).

EXAMPLE 18

1-sec.-butyl-2-(4-chlorobenzyl)perhydroazepine

Follow the procedure of Example 12 to obtain 3.2 g of the title compound from 5.0 g of the title compound of Example 10, 4.0 g of anhydrous potassium carbonate and 3.0 g of sec.-butyl bromide.

EXAMPLE 19

2-(4-chlorobenzyl)-1-neopentylperhydroazepine

Follow the procedure of Example 12 to obtain 3.9 g of the title compound from 5.0 g of the title compound of Example 10, 4.0 g of anhydrous potassium carbonate and 3.6 g of neopentyl bromide.

EXAMPLE 20

2-(4-chlorobenzyl)-1-cyclohexylperhydroazepine

Follow the procedure of Example 12 to obtain 2.35 g of the title compound from 5 g of the title compound of Example 10, 3.1 g of anhydrous potassium carbonate and 4 g of cyclohexyl bromide.

EXAMPLE 21

1-methyl-2-(4-nitrobenzyl)perhydroazepine

Follow the procedure of Example 12 to obtain 1.9 g of the title compound as a red oil from 2.34 g of the title compound of Example 16, 1.4 g of anhydrous potassium carbonate and 1.5 g of methyl iodide.

EXAMPLE 22

2-(4-aminobenzyl)-1-methylperhydroazepine

Follow the procedure of Example 17 to obtain 2.9 g of the oily title compound from 3.45 g of the title compound of Example 21 by hydrogenation with PtO$_2$/hydrogen.

EXAMPLE 23

2(4-diethylaminobenzyl)-1-methylperhydroazepine

Stir 2.18 g of the title compound of Example 22 and 2.0 g of anhydrous potassium carbonate with 3.1 g of diethyl sulfate at 140° for 7 hours and then cool to ambient temperature. Mix the resulting suspension with water and pour it into caustic soda solution before extracting it with diethyl ether. Dry the organic phase over sodium sulfate and distil off the ether to obtain 1.9 g (70% yield) of the title compound as residue.

EXAMPLE 24

2-benzyl-1-methylperhydroazepine

Follow the procedure of Example 12 to obtain 2.4 g (56% of theory) of the title compound with a BP of 68° at 0.003 mm of Hg from 4.0 g of 2-benzylperhydroazepine (the title compound of Example 11), 2.9 g of anhydrous potassium carbonate and 3.3 g of methyl iodide.

The picrate melts at 116° to 188°.

EXAMPLE 25

2-(4-bromobenzyl)-1-methylperhydroazepine

Mix 2.03 g of the title compound of Example 24 and 50 mg of iron powder with 10 m moles of bromine at room temperature and stir the resulting reaction mixture for 2 hours. Alkalize this reaction mixture with caustic soda solution and then extract the base with diethyl ether. Distil the ether extract to obtain the title compound as an oily and almost colorless liquid with a BP of 108° at 0.003 mm of Hg.

EXAMPLE 26

2-(3,4-dihydroxybenzyl)-1-methylperhydroazepine

Boil a mixture of 5.0 g of the title compound of Example 7, 45 ml of acetic acid and 45 ml of 48% hydrobromic acid for 40 hours under reflux. Remove the bulk of the acid from the resulting reaction mixture by distilling the reaction mixture in vacuo. Take up the residue with iced water and alkalize with soda solution. Extract the thus-produced base for several hours with diethyl ether and then distil off the ether to obtain 4.0 g of the title compound as residue. Convert the residue into 3.0 g of the hydrochloride with methyl alcohol/diethyl ether/hydrochloric acid.

EXAMPLE 27

2-(α-ethoxycarbonyl-3,4,5-trimethoxybenzylidene)-1-methylperhydroazepine

Follow the procedure of Example 2 to obtain 14.3 g (28% of theory) of the title compound as a viscous oil from 50 g of the title compound of Example 1, 35.6 of ethyl 3,4,5-trimethoxyphenylacetate and a solution of 4.32 g of sodium in 100 ml of ethanol.

EXAMPLE 28

2-benzyl-1-cyclopropylcarbonylperhydroazepine

Add (drop by drop at from 0° to 8° ) 4.3 g of cyclopropane carboxylic acid chloride in 40 ml of dichloromethane to 7.0 g of the title compound of Example 11 and 4.1 g of triethylamine in 70 ml of dichloromethane. Continue stirring for a further 2 hours at 0°, and then mix the thus-prepared reaction mixture with 300 ml of water. Separate the organic phase and extract the aqueous phase again with dichloromethane. Combine the organic phases and wash them with dilute hydrochloric acid and soda solution. Dry the thus-washed organic phases over sodium sulfate and concentrate the resultant to obtain 9.2 g (97% of theory) of the title compound as viscous oil.

EXAMPLE 29

2-benzyl-1-cyclopropylmethylperhydroazepine

Dissolve in 9.0 g of the title compound of Example 28 in 80 ml of tetrahydrofuran. Add the resulting solution (drop by drop over a period of 10 minutes while stirring at 0°) to a suspension of 1.30 g of lithium aluminum hydride (=lithium hydridoaluminate) in 30 ml of tetrahydrofuran. Then boil the prepared admixture for 1.5 hours under reflux before adding a further 2.0 g of lithium aluminum hydride thereto and boiling for a further 3.5 hours under reflux. Cool the refluxed product to ambient temperature. Carefully add 300 ml of water to the cooled material and extract it 3 times with 50 ml of diethyl ether (each time). Wash the combined ether solutions with saturated common salt solution. Dry the washed solutions over sodium sulfate. Evaporate off the solvent in vacuo. Distil the residue to obtain 5.89 g of the title compound with a BP at 115° at 0.01 mm of Hg.

EXAMPLE 30

1-acetyl-2-benzylperhydroazepine

Follow the procedure of Example 28 to obtain 5.8 g of the title compound as a viscous oil from 6 g of 2-benzylperhydroazepine, 4.14 g of triethylamine and 2.65 g of acetyl chloride.

EXAMPLE 31

1-ethyl-2-benzyperhydroazepine

Follow the procedure of Example 29 to obtain 1.2 g of the title compound as an oil with a BP of 90° to 95° at 0.008 mm of Hg from 2.5 g of the title compound of Example 30 and 0.80 g of lithium aluminum hydride.

EXAMPLE 32

2-(4-chlorobenzyl)-1-cyclopropylcarbonylperhydroazepine

Follow the procedure of Example 28 to obtain 6.2 g of the title compound as a viscous light yellow oil from 6 g of the title compound of Example 10, 4.14 g of triethylamine and 4.30 g of cyclopropanecarboxylic acid chloride.

EXAMPLE 33

2-(4-chlorobenzyl)-1-cyclopropylmethylperhydroazepine

Follow the procedure of Example 29 to obtain 3.2 g of the title compound as a colorless oily liquid with a BP of 100° to 105° at 0.01 mm of Hg from 5.0 g of the title compound of Example 32 and 1.4 g of lithium aluminum hydride.

EXAMPLE 24

2-(4-acetylaminobenzyl)-1-methylperhydroazepine

Add a solution of 0.75 g of acetyl chloride in 5 ml of benzene drop by drop to a solution of 1.9 g of the title compound of Example 22 and 1 g of triethylamine in 10 ml of benzene. After an hour concentrate the resulting product, take it up with water and diethyl ether, collect the organic phase and concentrate it to obtain the title compound.

EXAMPLE 35

2-(4-methoxybenzyl)perhydroazepine

Stir 6.5 g of caprolactim methyl ether, 5.0 g of 4-methoxybenzyl cyanide and 0.5 g of 1,5-diazabicyclo[5.4.0]-undec-5-ene together under nitrogen for 18 hours at 125°. Then remove volatile components from the resulting reaction mixture under a high vacuum to obtain 2-(α-cyano-4-methoxybenzylidene)perhydroazepine as a viscous dark residue. Boil this residue with 50 ml of concentrated hydrochloric acid under reflux until the evolution of carbon dioxide ceases. Cool the refluxed material to ambient temperature, and then alkalize it (while cooling), extract the produced base with diethyl ether, dry the ether extract over sodium sulfate and concentrate the dried extract to obtain 2-(4-methoxybenzyl)-4,5,6,7-tetrahydro-3H-azepine. Hydrogenate this intermediate with platinum/active carbon/hydrogen in ethyl alcohol, filter off the catalyst, concentrate and then distil the filtrate to obtain the title compound with a BP of 100° to 106° at 0.01 mm of Hg.

EXAMPLE 36

2-(3-methoxybenzyl)perhydroazepine

Follow the procedure of Example 35 to obtain the title compound as an oil with a BP of 98° to 103° at 0.01 mm of Hg from caprolactim methyl ether, 3-methoxybenzyl cyanide and 1,5-diazabicyclo[5.4.0]undec-5-ene.

EXAMPLE 37

2-(4-methoxybenzyl)-1-methlperhydroazepine

Follow the procedure of Example 12 to obtain the title compound as a light-colored oil from 2.19 g of the title compound of Example 35, 2.9 g of methyl idodide and 2.1 g of anhydrous potassium carbonate.

EXAMPLE 38

2-(3-methoxybenzyl)-1-methylperhydroazepine

Follow the procedure of Example 12 to obtain the title compound as an oil with a BP of 110° to 115° at 0.01 mm of Hg from the title compound of Example 36, methyl iodide and potassium carbonate.

EXAMPLE 39

2-(4-chlorobenzyl)-1-[3-(4-fluorobenzoyl)propyl]perhydroazepine

Boil 2 g of the title compound of Example 10, 2.7 g of ω-chloro-4-fluorobutyrophenone, 1.89 g of potassium carbonate and 10 ml of methylethylketone together under reflux for 70 hours. Cool the resulting reaction mixture to ambient temperature. Mix the cooled mixture with 25 ml of water and 25 ml of diethyl ether. Collect the ether phase. Dry it over sodium sulfate, concentrate it and then further dry it under a high vacuum at 80° to obtain 1.0 g of the title compound as a viscous light-brown oil.

EXAMPLE 40

2-(4-chlorobenzyl)-1-[4-(4-fluorophenyl)butyl]perhydroazepine

Heat 0.5 g of the title compound of Example 39 with 1 ml of hydrazine hydrate, 0.5 g of potassium hydroxide and 5 ml of triglycol for 2 hours at 165°. Cool the resulting reaction mixture to ambient temperature. Mix the cooled reaction mixture with water and diethyl ether. Dry the ether phase over sodium sulfate and then concentrate it to obtain 0.3 g of the title compound as a viscous oil.

EXAMPLE 41

1-benzyl-2-(4-chlorobenzyl)perhydroazepine

Follow the procedure of Example 12 to obtain 3.95 g of the oily title compound from 5 g of the title compound of Example 10, 3.2 g of anhydrous potassium carbonate and 2.83 g of benzyl chloride.

EXAMPLE 42

2-(4-chlorobenzyl)perhydroazepine

Hydrogenate 3.0 g of the title compound of Example 41 in 50 ml of ethyl alcohol with 10% of palladium on active carbon. Then filter off the catalyst, concentrate the filtrate and convert the residue into the hydrochloride with ethereal hydrochloride acid. Recrystallize the obtained hydrochloride (MP 176° to 178°) of the title compound from methyl alcohol/diethyl ether.

EXAMPLE 43

2-(4-chlorobenzyl)perhydroazepine

Boil 4.0 g of the title compound of Example 6 under reflux for 5 hours with 20 ml of ethyl chloroformate. Distil off the excess chloroformate ester and boil the residual crude 1-ethoxycarbonyl-2-(4-chlorobenzyl)perhydroazepine with 100 ml of n-butanol and 8 g of potassium hydroxide for 20 hours. Mix the produced reaction product with water and separate the organic phase. Extract the aqueous phase with dichloromethane. Combine and concentrate the organic phases. Convert the oily residue (the title compound) into the hydrochloride with ethereal hydrochloric acid. Recrystallize the hydrochloride from methyl alcohol/diethyl ether to obtain 2.2 g (50% of theory) of the hydrochloride, MP 177° to 178°.

Analogously, react the title compound of Example 41 with ethyl chloroformate and saponify the resulting reaction product with potassium hydroxide in butyl alcohol to obtain the title compound.

EXAMPLE 44

2(α-cyano-2-chlorobenzylidene)perhydroazepine

Follow the procedure of Example 9 to obtain 4.5 g of the oily title compound from 5.0 g of 2-chlorobenzyl cyanide, 5.5 g of caprolactim methyl ether and 0.5 g of diazabicyclo[5.4.0]-undec-5-ene.

EXAMPLE 45

2-(2-chlorobenzyl)perhydroazepine

Follow the procedure of Example 10 to obtain 1.9 g (52% of theory) of the title compound with a BP of 100° to 106° at 0.05 mm of HG from 4.0 g of the title compound of Example 44.

EXAMPLE 46

2-(α-cyano-3-chlorobenzylidene)perhydroazepine

Follow the procedure of Example 9 to obtain 4.5 g of the oily title compound from 5.0 g of 3-chlorobenzyl cyanide, 5.5 g of caprolactim methyl ether and 0.5 g of diazabicyclo[5.4.0]undec-5-ene.

EXAMPLE 47

2-(3-chlorobenzyl)perhydroazepine

Follow the procedure of Example 10 to obtain 2.2 g (60% in theory) of the title compound with a BP of 98° to 103° at 0.01 mm of Hg from 4.0 g of 2-[α-cyano-3-chloro benzylidene]perhydroazepine.

EXAMPLE 48

2-(3-chlorobenzyl)-1-methylperhydroazepine

Follow the procedure of Example 12 to obtain 2.0 g of the title compound from 2.5 g of the title compound of Example 47, 1.5 g of anhydrous potassium carbonate and 1.5 g of methyl iodide.

EXAMPLE 49

2-(α-ethoxycarbonyl-2-chlorobenzylidene)-1-methylperhydroazepine

Follow the procedure of Example 2 to obtain the title compound as a dark viscous oil from 80.2 g of the title compound of Example 1 and 40 g of ethyl 2-chlorophenylacetate.

EXAMPLE 50

2(2-chlorobenzyl)-1-methylperhydroazepine

Follow the procedure of Example 6 to obtain the title compound as a light-colored oil with a BP of 134° at 0.01 mm of Hg from the title compound of Example 49.

The picrate (from ethyl alcohol) melts at 123° to 126°.

EXAMPLE 51

7-(4-chlorobenzyl)perhydroazepin-2-one

To an ice-cold solution of 4.47 g of 2-(4-chlorobenzyl)cyclohexanone in 100g of polyphosphoric acid add 2.6 g of sodium azide while stirring. Stir the mixture for another 1.5 hours at 0° and for a further 8 hours at room temperature, pour it into ice water and then extract it with methylene chloride. After drying the organic phase over sodium sulfate distill off the solvent to obtain 2.85 g of the title compound as a light brown oil.

EXAMPLE 52

2-(4-chlorobenzyl)perhydroazepine

Add 0.5 g of lithium aluminum hydride to a solution of 2.8 g 7-(4-chlorobenzyl)-perhydroazepin-2-one in 30 ml of tetrahydrofurane. Boil the mixture under reflux for 16 hours, cool it and then carefully treat it with ice-water. After extraction with diethyl ether, dry the extract over sodium sulfate concentrate the oily residue and distill in a vacuum to obtain 1.8 g of the title compound with a BP of 90° to 92° at 0.05 mm Hg.

EXAMPLE 53

2-(4aminobenzyl)perhydroazepine

Hydrogenate 3.72 of 7-(4-nitrobenzyl)perhydroazepin-2-one in 50 mls of ethyl alcohol with platinum/hydrogen. After the absorption of hydrogen has ceased, filter off the catalyst and concentrate the filtrate. Dissolve the thus obtained 7-(4-aminobenzyl)-perhydroazepin-2-one in tetrahydrofuran. Add 680 mg of lithium aluminum hydride and boil the mixture under reflux. After cooling, treat it with ice-water and extract it with diethyl Dry the organic phase over sodium sulphate and concentrate it to obtain 2.0 g of the brown oily title compound.

The benzoate (from isopropanol) melts at 186°to 189°(dec.)

EXAMPLE 54

2-(2-methoxybenzyl)perhydroazepine

Using the mode of operation described in Example 52 obtain 1.5 g of the title compound as oil with a BP of 95° to 100° at 0.01 mm Hg from 2.8 g of 7-(methoxybenzyl)-perhydroazepin-2-one and 0.5 g of lithium aluminum hydride.

EXAMPLE 55

2-(4-methylbenzyl)perhydroazepine

Using the mode of operation described in Example 52 obtain 1.6 g of the title compound as oil with a BP of 82° to 85° at 0.01 mm Hg from 2.8 g of 7-(4-methylbenzyl)perhydroazepin-2-one and 0.5 of g lithium aluminum hydride.

EXAMPLE 56

2-(4-chlorobenzyl)perhydroazepine

Add a solution of 10 mmol of n-butyllithium in n-hexane to a solution of 1.01 g of diisopropylamine in 100 ml of tetrahydrofuran at 78° and pass argon through it. Stir the mixture for 5 minutes at room temperature and then cool it down again to −78°. Add a solution of 1.28 g of n-nitrosoperhydroazepine and stir for 1 hour. Then add 4.1 g of 4-chlorobenzyl bromide in a small amount of diethyl ether. After stirring for another 5 hours at −78° add 5 ml of glacial acetic acid. Warm the mixture up to room temperature and pour it into 100 ml of dichloromethane-saturated sodium chloride solution. Free the organic phase from the solvent and then solve it in methanol. After addition of 2 g of freshly prepared Laney nickel, pass hydrogen through the solution while stirring vigorously. Filter off the catalyst, and wash the catalyst with methanol. Concentrate the methanolic filtrate. Treat the oily residue with ethanol-ethereal hydrochloric acid to obtain the hydrochloride of the title compound: m.p. 176° to 178°.

EXAMPLE 57

Charge for 100 liters (ampoules)

| | | |
|---|---|---|
| 1. | 2-(4-chlorobenzyl)-1-isopropylperhydroazepine | 2.500 kg |
| 2. | Mannitol | 4.000 kg |
| 3. | Double-distilled water | up to 100 liters |

Dissolve 1 in about 80 liters of water under addition of an equivalent amount of hydrochloric acid and then add 2 to the resulting solution. Adjust the pH of the solution to 7.0±0.5 and then add the rest of the water. Filter (sterile) the solution over a filter and charge it into 2-ml ampoules under germ-free conditions.

EXAMPLE 58

Charge for tablets

| | | |
|---|---|---|
| 1. | 2-(4-chlorobenzyl)perhydroazepine hydrochloride | 10.0 kg |
| 2. | Glutamic acid | 5.0 kg |
| 3. | Maize starch | 38.0 kg |
| 4. | Milk sugar | 37.0 kg |
| 5. | Aerosil (submicroscopic pyrogenic silica) | 1.5 kg |
| 6. | Sodium lauryl sulfate | 2.0 kg |
| 7. | Gelatin | 2.5 kg |
| 8. | Glycerin | 0.5 kg |
| 9. | Talcum | 2.5 kg |
| 10. | Magnesium stearate | 1.0 kg |

Mix 2 with 5 kg of 4 and finely grind the admixture. Mix the admixture with 1, with 30 kg of 3 and with the rest of 4, 5 and 6; then sift the resultant. Moisten the sifted product with a solution of 7 and 8 in 35 liters of water and then pass it through a strainer with a mesh of 1.25 mm. Dry the strained material and mix the thus-prepared granulate with the rest of 3, 9 and 10 before pressing it into 200-mg tablets.

EXAMPLE 59

Charge for tablets

| | | |
|---|---|---|
| 1. | 2-(4-aminobenzyl)perhydroazepine benzoate | 30.0 kg |
| 2. | cellulose (Rehocel ®) | 8.5 kg |
| 3. | Milk sugar | 25.9 kg |
| 4. | Maize starch | 22.2 kg |
| 5. | polyvinylpyrrolidone (Kollidon ®25) | 3.0 kg |
| 6. | carboxymethylcellulose (Primojel) | 8.5 kg |
| 7. | Talcum | 2.5 kg |
| 8. | Magnesium stearate | 0.3 kg |

Mix 1, 2, 3 and 4, moisten the thus-prepared admixture with 5 (dissolved in 15 liters of water) and granulate. Pre-dry the granulate in a drying oven at 50° and then pass it through a sieve. Dry the granulate to a relative moisture content of from 45 to 50%, add 6, 7 and 8 thereto and carefully mix the resulting product before pressing it into 100-mg tablets.

EXAMPLE 60

Charge for tablets

| | | |
|---|---|---|
| 1. | 2-(4-chlorobenzyl)perhydroazepine hydrochloride | 25.0 kg |
| 2. | Rehocel | 8.5 kg |
| 3. | Milk sugar | 30.0 kg |
| 4. | Maize starch | 22.2 kg |
| 5. | Kollidon ®25 | 3.0 kg |
| 6. | Primojel | 8.5 kg |
| 7. | Talcum | 2.5 kg |
| 8. | Magnesium stearate | 0.3 kg |

Mix 1, 2, 3 and 4, moisten the thus-produced admixture with 5 (dissolved in 15 liters of water) and granulate. Pre-dry the granulate in a drying cabinet at 50= and then pass it through a sieve. Dry the granulate to a relative moisture content of from 45 to 50%. Then add 6, 7 and 8 thereto, mix carefully and press the obtained mixture into 100-mg tablets.

The invention and its advantages are readily appreciated by those of ordinary skill in the art from the preceding description and illustrative examples. It is readily apparent that various structural changes may be made in the compounds, and various compounding and formulation changes many be made in the compositions without departing from the spirit or scope of the invention or sacrificing its material advantages. The herein-specified compounds, delineated procedures and provided examples are merely examplary of preferred embodiments.

What is claimed is:

1. A compound which, in free-base form, is one of the formulae:

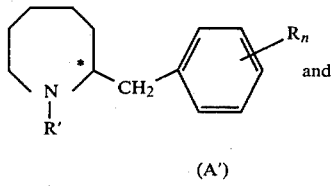

(A')

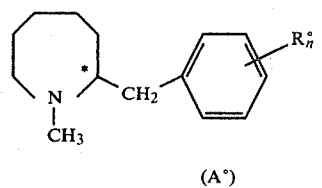

(A°)

wherein
R' is a member selected from the group consisting of lower aliphatic hydrocarbyl having more than one carbon atom, alicyclic hydrocarbyl having from 3 to 7 ring carbon atoms, optionally-substituted monoar (lower) alkyl and cycloalkyl(lower)alkyl;
each
R° is, independently, a member selected from the group consisting of halo, lower alkyl, —OH, lower alkoxy, [lower]lower alkanoyloxy [c]y, —NH$_2$, monosubstituted amino, disubstituted amino, —NO$_2$, phenyl and substituted phenyl; or two, bound to adjacent ring carbon atoms, are jointly alkylenedioxy having from 1 to 4 carbon atoms;
each
R is —H, one of the independent meanings of R° or, together with another R, bound to an adjacent ring carbon atom, alkylenedioxy having from 1 to 4 carbon atoms;
n is a positive whole number of at most 4;
wherein ar(lower)alkyl is aryl-substituted lower alkyl wherein the aryl is a substituted or unsubstituted monovalent unsaturated aromatic carbocyclic radical having a single ring or two or three condensed rings having a total of at most 12 ring members, each aromatic ring having from 5 to 7 ring members; and wherein any substituent bound to an aromatic carbon atom is a member selected from the group consisting of halo, lower alkyl, —OH, lower alkoxy, lower alkylenedioxy, lower alkanoyloxy, —NH$_2$, monosubstituted amino, disubstituted amino, —NO$_2$, and phenyl; any substituent bound to an aliphatic carbon atom of an araliphatic radical is a member selected from the group consisting of —OH and oxo; and any substituent of monosubstituted or of disubstituted amino is, independently, a member selected from the group consisting of alkanoyl having from 2 to 5 carbon atoms and lower alkyl.

2. A compound according to claim 1 which is a member selected from the group consisting of (a) a compound of the formula

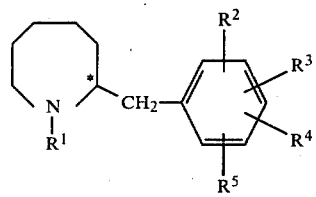

wherein
R$^1$ is lower aliphatic hydrocarbyl having at least 2 carbon atoms, alicyclic hydrocarbyl having from 3 to 7 ring carbon atoms, cycloaklyl(lower)alkyl having from 3 to 7 ring carbon atoms, homocyclic ar(lower)alkyl or substituted homocyclic ar(lower)alkyl;
R$^2$ is —H, halo, lower alkyl, —OH, lower alkoxy, lower alkanoyloxy, —NH$_2$, mono-substituted amino, disubtituted amino, —NO$_2$, phenyl or substituted phenyl;
R$^3$ is —H, halo, lower alkyl, —OH, lower alkoxy, lower alkanoyloxy, —NH$_2$, mono-substituted amino, disubtituted amino, —NO$_2$, phenyl or substituted phenyl; or
R$^2$ and R$^3$, bound to adjacent ring carbon atoms, are jointly alkylenedioxy having from 1 to 4 carbon atoms;
R$^4$ is —H, halo, lower alkyl, —OH, lower alkoxy, lower alkanoyloxy, —NH$_2$, monosubstituted amino, disubtituted amino, —NO$_2$, phenyl or substituted phenyl; and
R$^5$ is —H, halo, lower alkyl, —OH, lower alkoxy, lower alkanoyloxy, —NH$_2$, monosubstituted amino, disubtituted amino, —NO$_2$, phenyl or substituted phenyl; or $R^4$ and $R^5$, bound to adjacent ring carbon atoms, are jointly alkylenedioxy having from 1 to 4 carbon atoms; and (b) a pharmacologically-acceptable acid-addition salt of (a).

3. A physiologically-acceptable and pharmacologically-active compound according to claim 2 wherein the 2- and/or the 6-position of the benzyl nucleus is unsubstituted.

4. A process which comprises administering an analgesic-effective amount of a compound according claim 3 to a warm-blooded animal afflicted with pain.

5. A compound according to claim 3 wherein $R^1$ is lower aliphatic hydrocarbyl.

6. A compound according to claim 3 wherein $R^1$ is alicyclic hydrocarbyl.

7. A compound according to claim 3 wherein $R^1$ is cycloalkyl(lower)alkyl.

8. A compound according to claim 3 wherein $R^1$ is optionally-substituted ar(lower)alkyl.

9. A compound according to claim 3 wherein $R^2$ is —H.

10. A compound according to claim 3 wherein $R^2$ is halo.

11. A compound according to claim 3 wherein $R^2$ is lower alkyl.

12. A compound according to claim 3 wherein $R^2$ is —OH.

13. A compound according to claim 3 wherein $R^2$ is lower alkoxy.

14. A compound according to claim 3 wherein $R^2$ is lower alkanoyloxy.

15. A compound according to claim 3 wherein $R^2$ is optionally-substituted amino.

16. A compound according to claim 3 wherein $R^2$ is —NO$_2$.

17. A compound according to claim 3 wherein $R^2$ is optionally-substituted phenyl.

18. A compound according to claim 3 wherein $R^2$ and $R^3$, jointly, are lower akylenedioxy.

19. A compound according to claim 3 wherein $R^1$ is lower aliphatic hydrocarbyl having at least 3 carbon atoms.

20. A compound according to claim 3 wherein
$R^1$ is straight-chained or branched aliphatic hydrocarbyl with from 1 to 6 carbon atoms, cycloalkylalkyl with 1 or 2 carbon atoms in the alkyl and from 3 to 5 ring carbon atoms in the cycloalkyl, phenalkyl with from 1 to 4 alkyl carbon atoms or monosubstituted phenalkyl with from 1 to 4 carbon atoms in the alkyl;
$R^2$ is halo, —OH, alkyl with from 1 to 4 carbon atoms, alkoxy with from 1 to 4 carbon atoms, alkanoyloxy with from 2 to 5 carbon atoms, —NH$_2$, dialkylamino with 1 or 2carbon atoms in each alkyl, —NO$_2$, phenyl or p-substituted phenyl; and each of
$R^3$, $R^4$ and $R^5$ is, independently, —H, halo, —OH, alkyl with from 1 to 4 carbon atoms, alkoxy with from 1 to 4 carbon atoms, alkanoyloxy with from 2 to 5 carbon atoms, —NH$_2$, dialkylamino with 1 or 2 carbon atoms in each alkyl or —NO$_2$.

21. A compound according to claim 20 wherein at least one of $R^3$, $R^4$ and $R^5$ is —H.

22. A compound according to claim 20 wherein at least each of two of $R^3$, $R^4$ and $R^5$ is —H.

23. A compound according to claim 20 wherein
$R^1$ is straight-chained alkyl with 2 or 3 carbon atoms, branched alkyl with from 3 to 5 carbon atoms, cycloalkylmethyl with from 3 to 5 ring carbon atoms, benzyl, p-halobenzyl, p-methoxybenzyl or p-methyoxybenzyl;
$R^2$ is halo, —OH, methoxy, —NH$_2$ or —NO$_2$;
$R^3$ is —H, halo, —OH, methoxy, —NH$_2$ or —NO$_2$; and each of $R^4$ and $R^5$ is —H.

24. A compound according to claim 23 wherein each of $R^2$ and $R^3$ is in the 2-position, the 3-position or the 4-position on the benzyl nucleus.

25. A compound according to claim 24 wherein $R^1$ is methyl, isopropyl, cyclopropylmethyl or benzyl.

26. A compound according to claim 25 wherein
$R^1$ is —H, methyl, isopropyl or cyclopropylmethyl;
$R^2$ is 2-chloro, 3-chloro, 4-chloro or 4-amino; and
$R^3$ is —H.

27. A compound according to claim 3 wherein
$R^1$ is, straight chained or branched aliphatic hydrocarbyl with from 2 to 6 carbon atoms, cycloalkylalkyl with 1 or 2 carbon atoms in the alkyl and from 3 to 5 ring carbon atoms in the cycloalkyl, phenalkyl with from 1 to 4 alkyl carbon atoms or monosubstituted phenalkyl with from 1 to 4 carbon atoms in the alkyl; and each of
$R^2$, $R^3$, $R^4$ and $R^5$ is, independently, —H, halo, —OH, alkyl having from 1 to 4 carbon atoms, alkoxy having from 1 to 4 carbon atoms, alkanoyloxy having from 2 to 5 carbon atoms, —NH$_2$, dialkylamino with 1 or 2 carbon atoms in each alkyl, —NO$_2$, phenyl or p-substituted phenyl.

28. A compound according to claim 27 wherein at least one of $R^3$, $R^4$ and $R^5$ is —H.

29. A compound according to claim 27 wherein at least each of two of $R^3$, $R^4$ and $R^5$ is —H.

30. A compound according to claim 29 wherein
$R^1$ is, straight-chained alkyl with 2 or 3 carbon atoms, branched alkyl with from 3 to 5 carbon atoms, cycloalkylmethyl with from 3 to 5 ring carbon atoms, benzyl, p-halobenzyl, p-methylbenzyl or p-methoxybenzyl; each of
$R^2$ and $R^3$ is, independently, —H, halo, —OH, methoxy, —NH$_2$ or —NO$_2$; and each of
$R^4$ and $R^5$ is —H.

31. A compound according to claim 30 wherein $R^1$ is ethyl, isopropyl, cyclopropylmethyl or benzyl.

32. A compound according to claim 3 which is 2-(2-chlorobenzyl)-1-methylperhydroazepine or a pharmacologically-tolerated acid-addition salt thereof.

33. A compound according to claim 27 wherein $R^2$, $R^3$, $R^4$ and $R^5$ is —H.

34. A compound according to claim 3 which is 2-(4-chlorobenzyl)-1-isopropylperhydroazepine or a pharmacologically-tolerated acid-addition salt thereof.

35. A compound according to claim 3 which is 2-(4-chlorobenzyl)-1-methylperhydroazepine or a pharmacologically-tolerated acid-addition salt thereof.

36. A compound which is 2-(4-aminobenzyl)perhydroazepine or a pharmacologically-tolerated acid-addition salt thereof.

37. A 2-benzylperhydroazepine according to claim 3 in the form of a racemate, an enantiomer or a mixture of enantiomers.

38. A medicament composition having active principle in combination with excipient or carrier and wherein the active principle comprises 1 to 200 milligrams of a compound according to claim 3 in a concentration which is within the range of from 5 to 95 percent by weight, based on the entire weight of the composition.

39. A process which comprises administering a blood-pressure lowering amount of a compound according to claim 3 to a warm-blooded animal afflicted with pathological blood pressure changes.

40. A process which comprises administering a CNS-stimulating amount of a compound according to claim 3 to a warm-blooded animal lacking vigilance or having pathologically-inhibited drive.

41. A compound according to claim 27 which is 2-benzyl-1-cyclopropylmethylperhydroazepin or a pharmacologically-tolerated acid-addition salt thereof.

42. A compound according to claim 1 of formula (A′).

43. A compound according to claim 1 of formula (A°).

44. A medicament composition having active principle in combination with excipient or carrier and wherein the active principle comprises 1 to 200 milligrams of a compound according to claim 36 in a concentration which is within the range of from 5 to 95 percent by weight, based on the entire weight of the composition.

45. A process which comprises administering a blood-pressure lowering amount of a compound according to claim 36 to a warm-blooded animal afflicted with pathological blood pressure changes.

46. A process which comprises administering a CNS-stimulating amount of a compound according to claim 36 to a warm-blooded animal lacking vigilance or having pathologically-inhibited drive.

47. A process which comprises administering an analgesic-effective amount of a compound according to claim 36 to a warm-blooded animal afflicted with pain.

* * * * *

UNITED STATES PATENT AND TRADEMARK OFFICE
CERTIFICATE OF CORRECTION

PATENT NO. : 4,221,788
DATED : September 9, 1980
INVENTOR(S) : KLAUS EISTETTER

It is certified that error appears in the above-identified patent and that said Letters Patent are hereby corrected as shown below:

Column 9, lines 50 to 55, between the structures designated (c) and (d) read --or--. Column 16, line 29, "III" should read --III,--. Column 20, line 28, "matrotilin" should read --maprotilin--. Column 23, line 24, "Pharmacodyne." should read --Pharmacodyn.--; line 37, "control...Pharmacodyn." should read --control.--. Column 24, lines 5 and 6, "determined...Ther.," should read --determined.--; lines 7 and 8, "[Koster...Writhing)" should read --test (acetic acid writhing) [Koster, Anderson and De Beer, Fed. Proc., 18, 412, 1959]--. Column 31, line 10 (title of Example 37), "methlperhydroazepine" should read --methylperhydroazepine--; line 14, "idodide" should read --iodide--. Column 32, line 50, "in" should read --of--. Column 33, line 25, "tetrahydrofurane" should read --tetrahydrofuran--; line 42, "diethyl" should read --diethyl ether.--. Column 34, line 6, "-78°" should read -- -78°,--; approximately line 63 (in the entry for the third ingredient) "25.9" should read --25.0--. Column 35, line 22, "50=" should read --50°--; line 39, "is one" should read --is of one--; lines 62 and 63, "monoar (lower) alkyl" should read --monoar(lower)alkyl--; line 67, "[lower ...[c]y" should read --lower alkanoyloxy--. Column 36, line 21, "-NO₂," should read -- -NO$_2$--; line 51, "disubtituted" should read --disubstituted--. Column 37, line 13, "R$^I$" should read --R$^1$--; line 56, "2carbon" should read --2 carbon --; line 57, "p-substituted" should read --*p*-substituted--. Column 38, line 4, "p-halobenzyl, p-methoxybenzyl" should read --*p*-halobenzyl, *p*-methylbenzyl--; line 5, "p-methyoxybenzyl" should read --*p*-methoxybenzyl--; line 15, "is -H," should read --is--; lines 20 and 39, "is," should read --is--; line 32, "p-substituted" should read --*p*-substituted--; line 42, "p-halobenzyl, p-methylbenzyl" should read --*p*-halobenzyl, *p*-methylbenzyl--; line 43, "p-methoxybenzyl" should

UNITED STATES PATENT AND TRADEMARK OFFICE
CERTIFICATE OF CORRECTION

PATENT NO. : 4,221,788

DATED : September 9, 1980

INVENTOR(S) : KLAUS EISTETTER

It is certified that error appears in the above-identified patent and that said Letters Patent are hereby corrected as shown below:

read --p-methoxybenzyl--.

Signed and Sealed this

Sixteenth Day of June 1981

[SEAL]

Attest:

RENE D. TEGTMEYER

Attesting Officer

Acting Commissioner of Patents and Trademarks